(12) United States Patent
Oe et al.

(10) Patent No.: US 9,075,003 B2
(45) Date of Patent: Jul. 7, 2015

(54) LIGHTING DEVICE, IMAGE ANALYSIS DEVICE, IMAGE ANALYSIS METHOD, AND EVALUATION METHOD

(75) Inventors: Mariko Oe, Kanagawa (JP); Kumiko Kikuchi, Kanagawa (JP); Motohiro Yanai, Kanagawa (JP); Yuji Masuda, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 543 days.

(21) Appl. No.: 13/582,086

(22) PCT Filed: Mar. 1, 2011

(86) PCT No.: PCT/JP2011/054613
§ 371 (c)(1),
(2), (4) Date: Aug. 31, 2012

(87) PCT Pub. No.: WO2011/111567
PCT Pub. Date: Sep. 15, 2011

(65) Prior Publication Data
US 2012/0327207 A1    Dec. 27, 2012

(30) Foreign Application Priority Data

Mar. 9, 2010 (JP) .................................. 2010-052189
Mar. 9, 2010 (JP) .................................. 2010-052190
Sep. 6, 2010 (JP) .................................. 2010-199388
Sep. 6, 2010 (JP) .................................. 2010-199389

(51) Int. Cl.
*G03B 29/00* (2006.01)
*G03B 41/00* (2006.01)
(Continued)

(52) U.S. Cl.
CPC ............ *G01N 21/359* (2013.01); *A61B 5/0064* (2013.01); *A61B 5/0075* (2013.01);
(Continued)

(58) Field of Classification Search
USPC .................................. 396/14; 382/118; 348/77
See application file for complete search history.

(56) References Cited

U.S. PATENT DOCUMENTS 3,330,193 A * 7/1967 Kaess .............................. 396/14
7,400,754 B2 * 7/2008 Jung et al. ..................... 382/128
(Continued)

FOREIGN PATENT DOCUMENTS

CN            1627317        6/2005
CN          200941278        8/2007
(Continued)

OTHER PUBLICATIONS

Extended European Search Report dated Jun. 27, 2014.
(Continued)

*Primary Examiner* — Clayton E Laballe
*Assistant Examiner* — Warren K Fenwick
(74) *Attorney, Agent, or Firm* — IPUSA, PLLC

(57) ABSTRACT

There is provided a lighting device for capturing a facial image of a subject by an image capturing unit in plural different near-infrared regions of light including a housing in which a substantially spherical space is formed by a spherical surface, the housing accommodating an entire face part of the subject; at least two light sources arranged at positions bilaterally symmetrical with the subject on the spherical surface to emit the light to light the substantially spherical space; an image capturing unit capturing an image of the entire face part; a first filter installed in front of the light source to block ultraviolet rays and infrared rays from the emitted light; a second filter installed in front of the lens to adjust an amount of the light, and a third filter installed in front of the lens to perform band-pass filtering corresponding to the different near-infrared regions.

16 Claims, 28 Drawing Sheets

(51) Int. Cl.
*G01N 21/359* (2014.01)
*A61B 5/00* (2006.01)
*G01N 21/47* (2006.01)
*G01N 21/3554* (2014.01)

(52) U.S. Cl.
CPC ............... *A61B 5/441* (2013.01); *A61B 5/443* (2013.01); *A61B 5/4875* (2013.01); *A61B 5/6814* (2013.01); *G01N 21/3554* (2013.01); *G01N 21/474* (2013.01); *G01N 2201/065* (2013.01)

(56) References Cited

U.S. PATENT DOCUMENTS

| | | | | |
|---|---|---|---|---|
| 2007/0212038 | A1* | 9/2007 | Asai et al. ...................... | 396/14 |
| 2008/0079843 | A1* | 4/2008 | Pote et al. ..................... | 348/371 |
| 2008/0212849 | A1* | 9/2008 | Gao ............................... | 382/118 |
| 2009/0134331 | A1  | 5/2009 | Miyamae et al. | |
| 2009/0226049 | A1* | 9/2009 | Debevec et al. .............. | 382/118 |

FOREIGN PATENT DOCUMENTS

| | | |
|---|---|---|
| CN | 101553819 | 10/2009 |
| EP | 1 433 418 A1 | 6/2004 |
| FR | 2930826 | 11/2009 |
| JP | 11-076173 | 3/1999 |
| JP | 2007-010584 | 1/2007 |
| JP | 2009-006089 | 1/2009 |
| JP | 2010-025622 | 2/2010 |
| WO | WO2005/099575 | 10/2005 |
| WO | WO2007/026884 | 3/2007 |
| WO | WO 2009/089292 A1 | 7/2009 |

OTHER PUBLICATIONS

Extended European Search Report mailed Jul. 19, 2013.
International Search Report mailed on Jun. 7, 2011.
Iwasaki Hiroaki et al., "Visualization for moisture of human face by spectroscopic imaging using two near-infrared bands", Optics Japan 2005 Tokyo, Optical Society of Japan (Japan Society of Applied Physics), Nov. 23-25, 2005.
M. Egawa, H. Arimoto, T. Hirao, M. Takahashi, and Y. Ozaki, Regional Difference of Water Content in Human Skin Studied by Diffuse-reflectance Near-infrared Spectroscopy-Consideration of Measurement Depth-, Appl Spectrosc, 60(1), 24-28(2006).
Chinese Office Action dated Jun. 18, 2014.

* cited by examiner

SIDE OF CAMERA

| | Right Side | Left Side |
|---|---|---|
| BEFORE COATING FD | SampleA | SampleB |
| COATING FD | FD OC10 | FD OC10 |
| CLEANSING | 2ml/cotton,10sec,tissue off | 2ml/cotton,10sec,tissue off |
| IMMEDIATELY AFTER CLEANSING | | |
| 15 MINUTES AFTER CLEANSING | | |

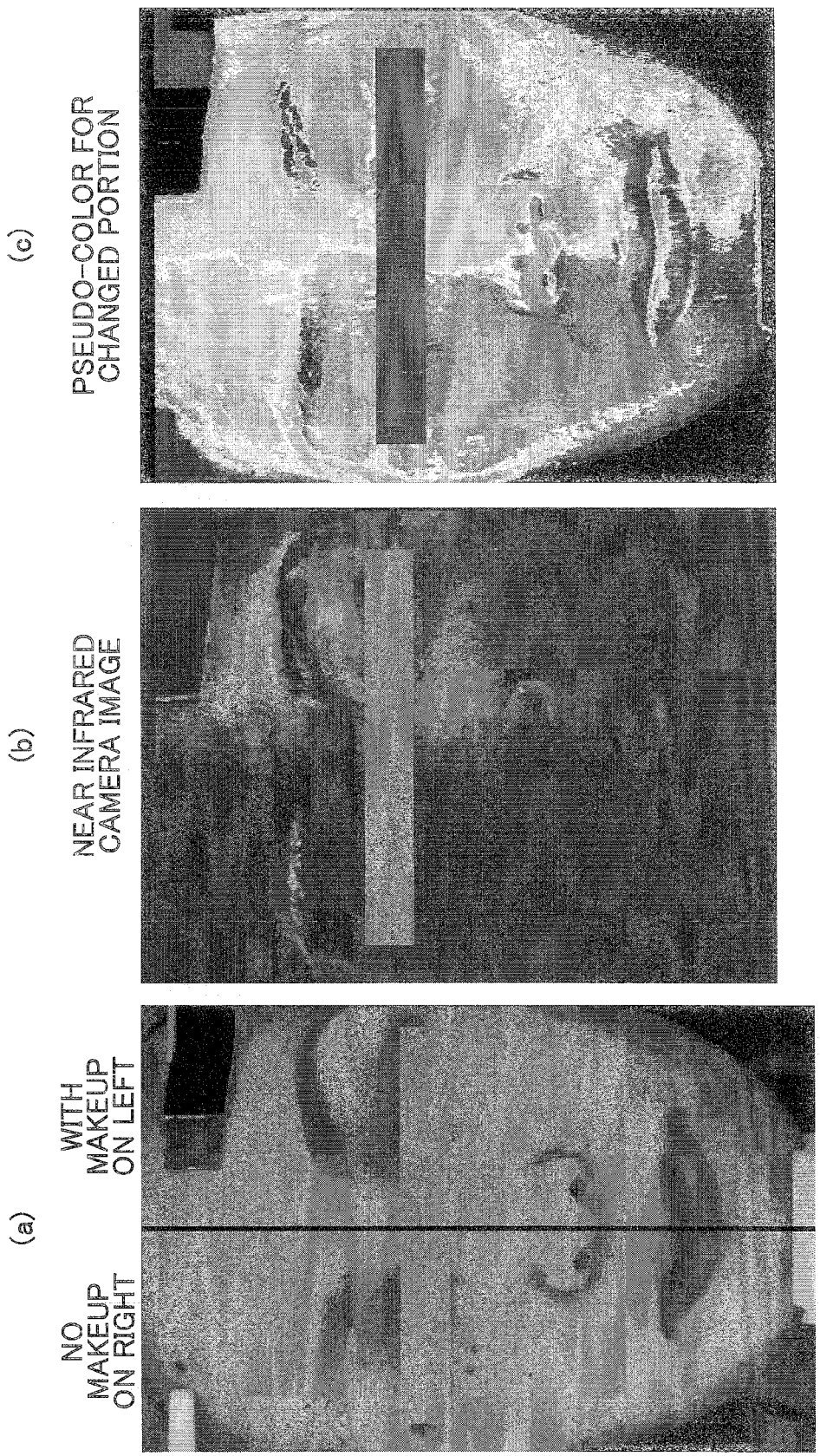

LIGHTING DEVICE, IMAGE ANALYSIS DEVICE, IMAGE ANALYSIS METHOD, AND EVALUATION METHOD

TECHNICAL FIELD

The present invention relates to a lighting device, an image analysis device, an image analysis method, and an evaluation method for accurately capturing an image on a near-infrared region.

BACKGROUND ART

Recently, there is disclosed a technique of visualizing moisturizer applied to a face using two near-infrared spectroscopic images captured by a near-infrared camera in order to visualize a moisture change on the face.

Non-Patent Document 1 uses an InGaAs near-infrared camera (SU320M-1.7RT, manufactured by Sensors Unlimited, Inc.) having a sensitivity of a wavelength of 900 nm to 1700 nm. The obtained two near-infrared spectroscopic images are converted to a differential extinction image to thereby visualize only the moisturizer applied to the face.

Further, a method of distinguishing a skin moisture using near-infrared is also disclosed in, for example, Patent Document 1.

The technique disclosed in Patent Document 1 includes a step of obtaining reflection intensity for a near-infrared wavelength region between 1050 nm to 1650 nm at plural points of a skin, a step of acquiring skin moisture at plural points on the skin by substituting reflection intensity of a prediction formula indicative of a relationship between the skin moisture and the near-infrared wavelength region for the reflection intensity obtained in the previous of obtaining reflection intensity, and a step of distinguishing a skin moisture distribution based on the skin moisture at the plural points of the skin. [Patent Document 1] Japanese Laid-open Patent Application Publication No. 2010-25622 [Non-Patent Document] Iwasaki Hiroaki et al., "Visualization for moisture of human face by spectroscopic imaging using two near-infrared bands", Optics Japan 2005 Tokyo, Optical Society of Japan (Japan Society of Applied Physics), Nov. 23-25, 2005.

DISCLOSURE OF THE INVENTION

Problems to be Solved by the Invention

In the above technique, a wavelength causing strong absorption by a face is 1460 nm and a wavelength causing no absorption by the face is 1060 nm. The wavelength region between 1050 nm and 1650 nm used in the Patent Document 1 is to focus attention on a near-infrared wavelength region before and after a wavelength of absorbing water near 1450 nm.

Water (OH radical) strongly absorbs light at around 1920 nm. Oil (CH radical) strongly absorbs light at around 1750 nm and around 2230 nm to 2400 nm. Although it is preferable to highly accurately capture an image of water or oil using the above characteristics, such a method is not devised yet. Although it is necessary to provide a lighting device for high accurately capture of an image on the above wavelengths, Patent Document 1 merely discloses a lighting mechanism for acquiring a color image for a ultraviolet region or a visible region. No technique is disclosed to irradiate a subject with a light source for the near-infrared region.

Although it is preferable to analyze or evaluate a skin, or counsel a skin care using plural portions of the skin strongly absorbing water or oil, such method is not disclosed.

The present invention is provided in consideration of the above problems. The objects of the present invention is to provide alighting device, an image analysis device, an image analysis method, and an evaluation method enabling analysis of a skin or the like using an image of the near-infrared region.

Means for Solving Problems

In order to solve the above problem, embodiments of the present invention may provide a lighting device for capturing a facial image of a subject by an image capturing unit in a plurality of different near-infrared regions of light including a housing in which a substantially spherical space is formed by a spherical surface, the housing being configured to accommodate an entire face part of the subject; at least two light sources arranged at positions bilaterally symmetrical with respect to the subject on the spherical surface to emit the light to light the substantially spherical space in the housing; an image capturing unit configured to capture an image of the entire face part lighted by the light; a first filter installed in front of the light source to block ultraviolet rays and infrared rays from the emitted light; a second filter installed in front of the lens of the image capturing unit to adjust an amount of the light, and a third filter installed in front of the lens of the image capturing unit to perform band-pass filtering corresponding to the plurality of different near-infrared regions.

Further, in order to solve the above problem, embodiments of the present invention may provide an image analysis device for analyzing the skin or hair of a subject using a facial image of the subject in a plurality of near-infrared regions captured by a lighting device including an image acquiring unit configured to acquire the facial images before and after coating with an external dermatological medication on the skin or the hair of the subject; a luminance correcting unit configured to correct luminance of the facial image acquired by the image acquiring unit; a difference amount acquiring unit configured to acquire difference amounts of the corrected facial images acquired by the luminance correcting unit before and after coating with the external dermatological medication on the skin or the hair of the subject in each of the plurality of near-infrared regions; an analyzing unit configured to analyze the skin and the hair of the subject based on the difference amounts acquired by the difference amount acquiring unit; and an image forming unit configured to generate an image for displaying a result of analysis acquired by the analyzing unit.

Further, in order to solve the above problem, embodiments of the present invention may provide an image analysis method for analyzing skin or hair of a subject using a facial image of the subject captured in a plurality of near-infrared regions including acquiring the facial images before and after coating with an external dermatological medication on the skin or the hair of the subject; correcting luminance of the facial image acquired by the acquiring the facial images; acquiring difference amounts of the corrected facial images acquired by the correcting before and after coating with the external dermatological medication on the skin or the hair of the subject in each of the plurality of near-infrared regions; analyzing the skin and the hair of the subject based on the difference amounts acquired by the acquiring the difference amounts; and generating an image for displaying a result of analysis acquired by the analyzing the skin and the hair.

Effect of the Invention

According to the embodiment of the present invention, it is possible to highly accurately analyze a moisture change of the skin of a subject and a change in adhesion of a cosmetic using an image of the near-infrared region.

BRIEF DESCRIPTION OF DRAWINGS

FIG. 28 illustrates exemplary images obtained under the conditions of the example 2.

BEST MODE FOR CARRYING OUT THE INVENTION

Preferred embodiments of the present invention are described next with reference to accompanying drawings.

The embodiment of the present invention relates to a lighting device for highly accurately acquiring desired images of various portions such a face, a hand, an arm and a hair of a subject using a near-infrared camera which can capture an image in a wavelength region of 800 nm to 2500 nm, and a lighting method using the lighting device. Specifically, images of the subject representing absorbing characteristics of water at around 1460 nm, absorbing characteristics of oil at around 1750 nm, strong absorbing characteristics of water at around 1920 nm, and strong absorbing characteristics of plural oils at around 2230 nm to 2400 nm are obtained. Based on the obtained images, moisture changes of the skin of the subject and changes of adhesion of cosmetics are analyzed and evaluated.

Figure 1:
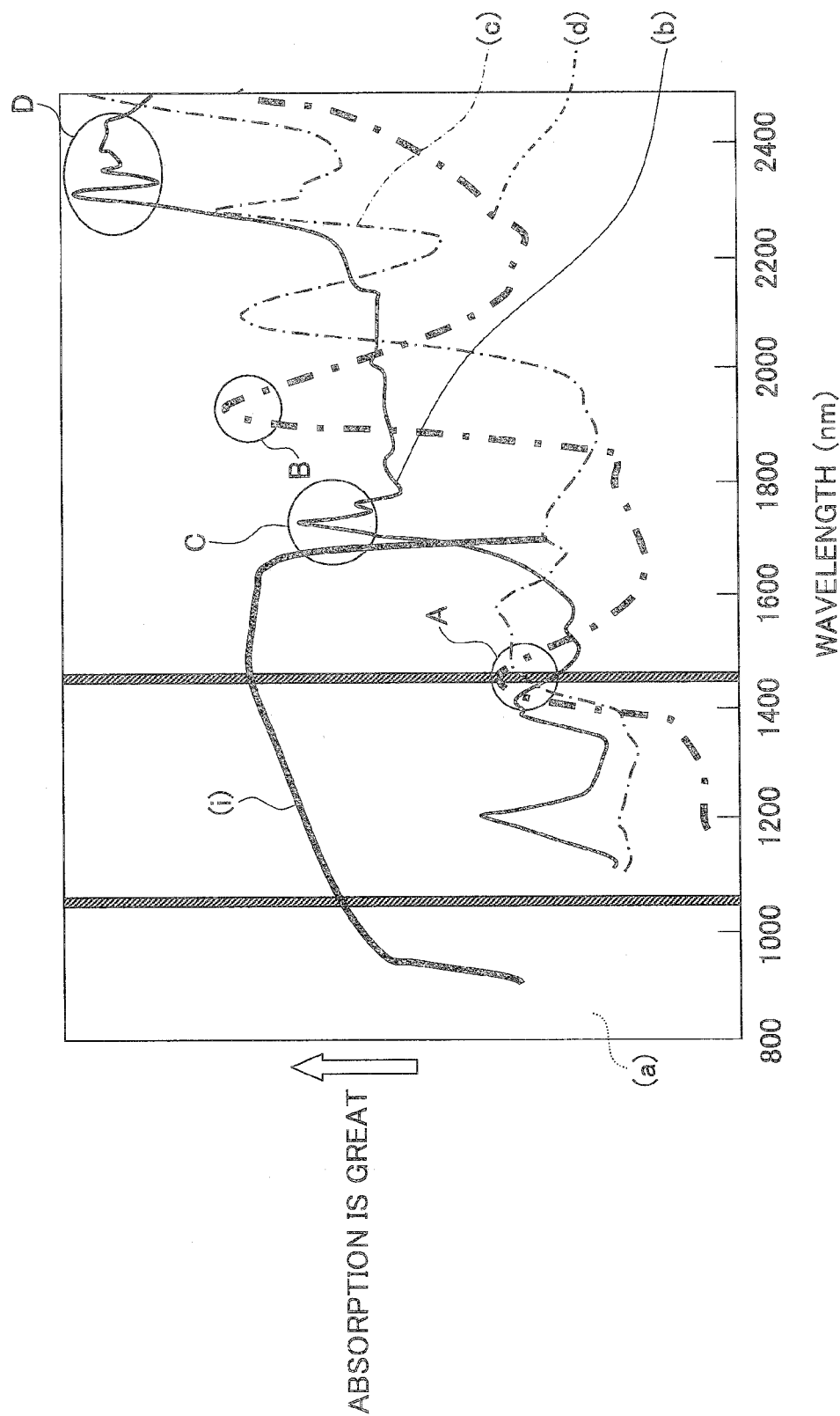
FIG. 1 illustrates exemplary absorbing characteristics of a skin in a near-infrared region.

FIG. 1 illustrates exemplary absorbing characteristics of the skin in a near-infrared region. Referring to FIG. 1, the abscissa of the graph represents a measured wavelength (nm) and the ordinate represents an absorbance (A/W).

FIG. 1 illustrates absorbing characteristics of water, palmitic acid, and glycerin for absorbing light having wavelengths at which images are captured. Referring to FIG. 1, (a) illustrates absorbing characteristics of water; (b) illustrates absorbing characteristics of palmitic acid; (c) illustrates absorbing characteristics of glycerin; and (d) illustrates absorbing characteristics of skin.

Referring to FIG. 1, (i) designates a near-infrared region in which an image can be captured by a commercially available camera such as an "ALPHA NIR camera" manufactured by FLIR Systems, Inc and "InGaAs Near Infrared Camera" manufactured by Xenics nv. Further, within the embodiment of the present invention, an image at a near-infrared region of about 1000 nm to about 2500 nm is captured by a camera manufactured by Sumitomo Electric Industries, Ltd.

Referring to FIG. 1, within a wavelength region captured by the commercially available camera, light having a wavelength of about 1460 nm is strongly absorbed by water (the region A in (d)). However, the region A overlaps peaks of the absorbing characteristics of oil (palmitic acid) and moisturizer (glycerin). Therefore, if a cosmetic is applied to a skin, analysis tends to be influenced by ingredients of the cosmetic. Therefore, accurate analysis of the skin may not be carried out by using the image in the above wavelength region.

Referring to FIG. 1, the line (d) illustrates absorbing characteristics of the skin in a region about 1920 nm are strong like the absorbing characteristics of the skin in the region about 1460 nm. The line (b) illustrates absorbing characteristics of the oil in a region about 1700 nm to about 1800 nm and strong absorbing characteristics of the oil in a region about 2230 nm to about 2400 nm.

Within the embodiment, it is possible to detect an image of water only in the wavelength region of about 1920 nm in addition to an image of water in the wavelength region of about 1460 nm. Thus, the images on the near-infrared region can be obtained. Further, within the embodiment, images of the oil in the wavelength region of about 1700 nm to about 1800 nm and in the wavelength region of about 2230 nm to about 2400 nm are obtained.

As described, both images of the water (OH radical) and the oil (CH radical) are obtained and one or both of the images are used for analysis to thereby display the skin coated with external dermatological medications such as lotion and emulsion. The displayed skin coated with the external dermatological medications can be used to evaluate uneven coating of the external dermatological medications.

Next, a structure of the lighting device for capturing the images is described. Hereinafter, an example of the skin is a face skin. However, the skin is not limited to the face skin and may be a hand skin, an arm skin, a skin substitute such as a swine skin, an artificial skin and urethane, hair, a nail, and various materials to be used for evaluating water and oil.

Figure 2:
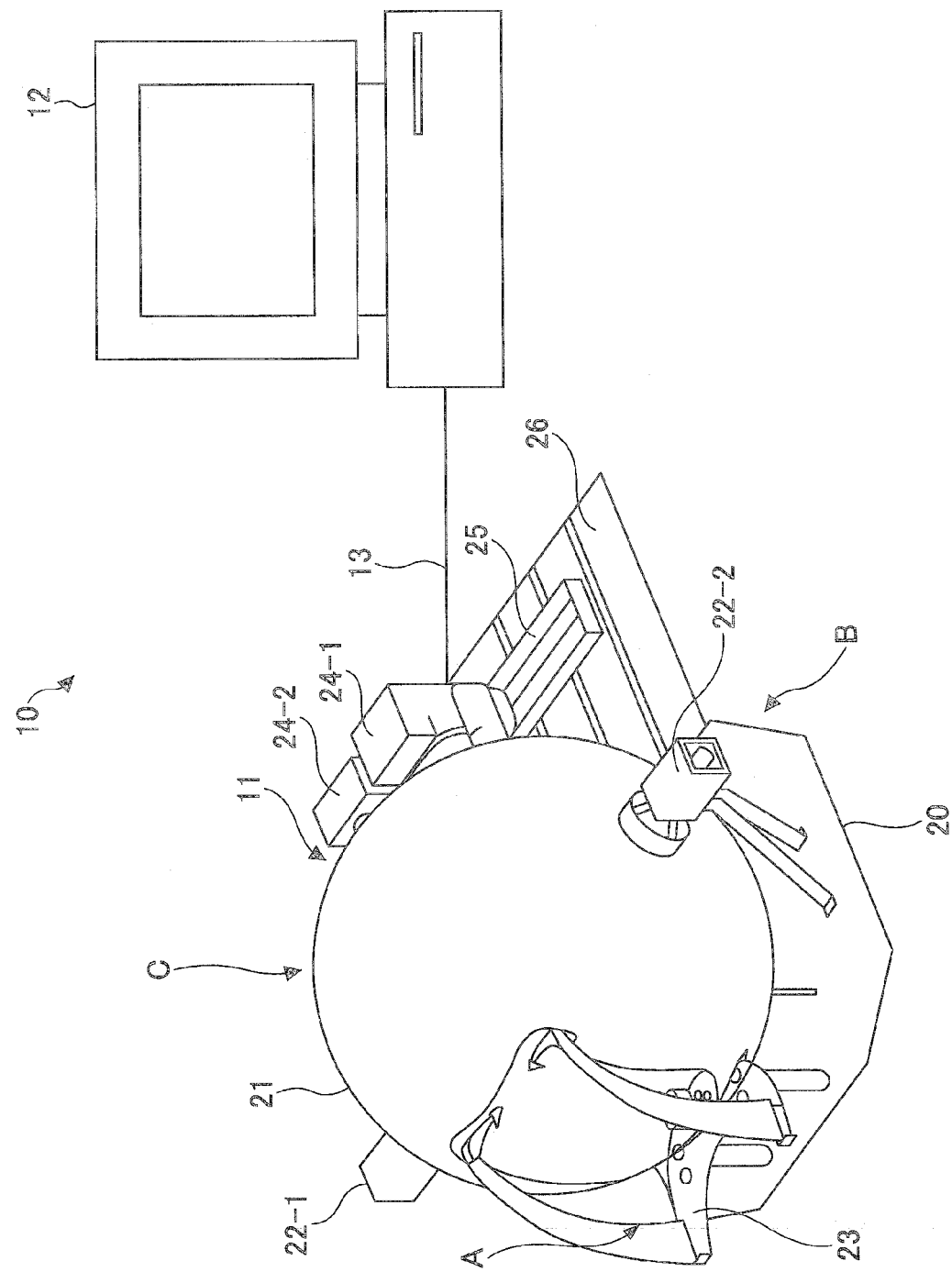
FIG. 2 illustrates a schematic structure of an exemplary lighting system of the embodiment.

FIG. 2 illustrates a schematic structure of the exemplary lighting system of the embodiment. The lighting system 10 includes a lighting device 11 and an image analysis device 12. The lighting device 11 and the image analysis device 12 are connected by a cable 13 and so on so that the lighting device 11 and the image analysis device 12 can mutually transmit and receive data and control signals.

The lighting device 11 receives the face of a subject to be analyzed. A predetermined portion of the face is irradiated by a light emitted from a predetermined light source inside a sphere formed in the lighting device 11. An image of the face is captured by a camera or the like. Within the embodiment, in order to obtain the facial images of the subject captured in plural different wavelength regions of the near-infrared region, a predetermined band-pass filter is used to filter the image. Thus, image data in the predetermined wavelength regions are obtainable.

Within the embodiment, when the facial image of the subject is captured by the lighting device 11, an image of a color chart is simultaneously captured. The color chart may be attached to or detached from the lighting device 11. Said differently, the captured image includes not only the face of the subject but also the color chart. The image of the color chart is used for correcting the captured image thereby improving an accuracy of reproduction of the facial image. The number of the color charts is one or plural. When there are plural color charts, the color chart corresponding to the wavelength of the light source can be selected and used.

Further, a polarizing filter or the like may be installed in the camera of the lighting device 11 thereby reducing noise. An exemplary lighting device 11 is described in detail later.

The image analysis device 12 receives images in the predetermined plural wavelength regions of the near-infrared region captured by the lighting device 11. The image analysis device 12 analyzes and evaluates water and oil on the skin of the subject on the images. With this, skin conditions and uneven coating of the external dermatological medication such as lotion and moisturizer can be visualized and output. Thus, highly accurate analysis and evaluation and display of the result become enabled. The image analysis device 12 of the embodiment functions as a skin analysis device to analyze skins. The image analysis device 12 is realized by a general-purpose computer.

The external dermatological medication may be of an aqueous system, a solubilized system, an emulsifying system, a powder dispersion system, a bi-layer system of water and oil, or a tri-layer system of water-oil-powder. The used application of the external dermatological medication is lotion, emulsion, basic skin care such as cream and face pack, makeup cosmetics such as lip stick and foundation, head hair care products such as shampoo, rinse, and hairdye.

Next, the exemplary lightning device 11 is described.

Figure 3A:
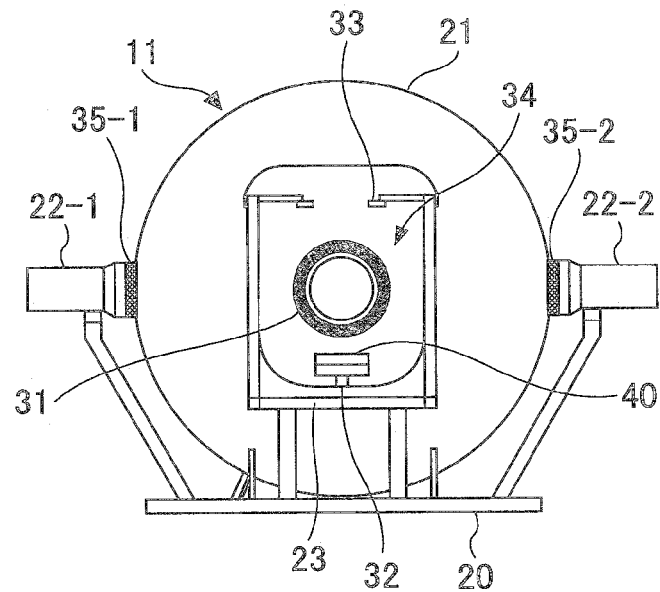
FIG. 3A illustrates an exemplary structure of the lighting device illustrated in FIG. 2.
Figure 3B:
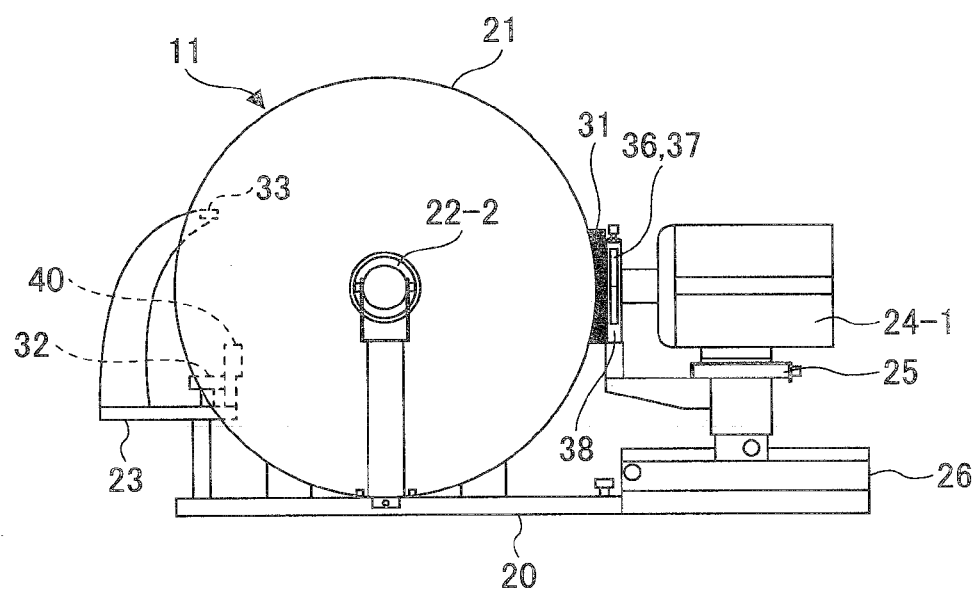
FIG. 3B illustrates an exemplary structure of the lighting device illustrated in FIG. 2.
Figure 3C:
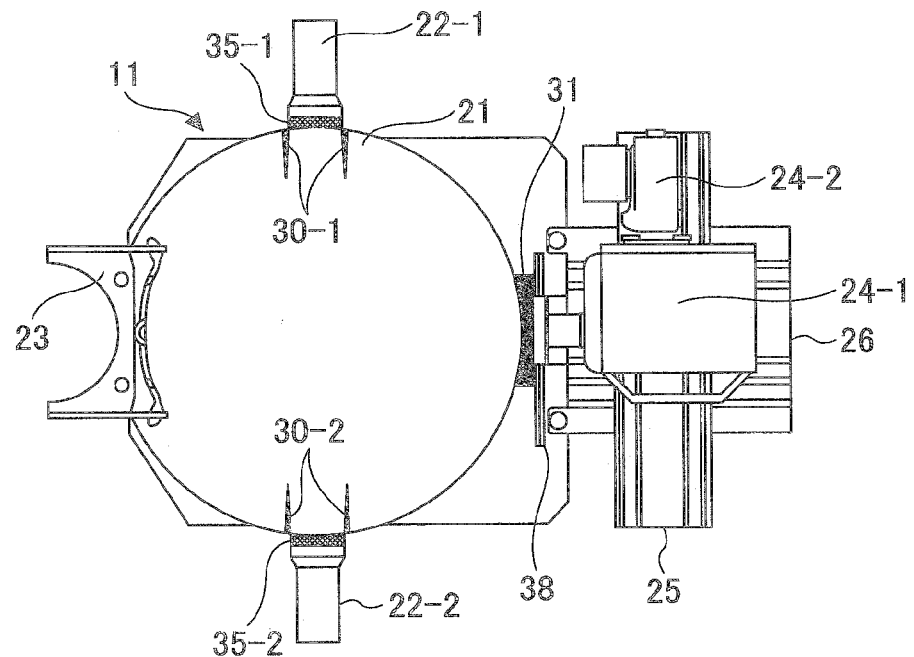
FIG. 3C illustrates an exemplary structure of the lighting device illustrated in FIG. 2.

FIGS. 3A, 3B and 3C specifically illustrate the structure of the lighting device 11 illustrated in FIG. 2. FIGS. 3A, 3B and 3C are viewed from arrows A, B and C in FIG. 2, respectively.

The lighting device 11 includes a base 20, a dome (housing) substantially shaped like a sphere and formed on the base 20, at least one light source 22, a chin rest 23, a camera 24 as an image capturing apparatus, a slide rail as a slide mechanism, and a camera platform 26, as a part of the structure.

Referring to FIGS. 2 and 3A to 3C, the dome 21 is substantially shaped like a sphere. The inside of the dome 21 is hollow. For example, the dome 21 has a diameter of about 40 cm to 90 cm so as to accommodate the face of a subject (a person). By shaping the dome 21 spherically, the light emitted from the light source diffuses and efficiently irradiates the face of the subject with even and flat light. With the embodiment, by causing the shape of the dome to be an integrating sphere, it is possible to suppress regular reflection light (shine) on a surface of the skin of the subject to thereby capture a highly accurate image.

The material of the dome 21 may be foam polystyrene, resin or the like. However, the embodiment is not specifically limited to this as long as light is diffused inside the dome 21 and efficiently and evenly irradiates the face of the subject.

For example, the inner surface (a reflection surface and a diffusion surface) of the dome 21 maybe a regular reflective material such as a silver surface, an electrolytic polishing surface of special aluminum alloy, a glass mirror surface (aluminum alloy), mercury, gold, platinum, and copper or magnesium carbonate, barium sulphate, alumina, white paint, enamel, blank sheet of paper, white tile or the like. Within the embodiment, the inner surface of the dome 21 may be coated several times by the same paint.

In coating inside the dome 21, the paint maybe of a spray type or a pen type. Further, the paint maybe of an acrylic system, a lacquer system, an enamel system or the like. For example, paints having different compositions of about 5 compositions may be prepared. One of the paints having a small variation of spectral reflectance and a high reflectance throughout the near-infrared region may be selected.

The inner surface of the dome 21 is preferably formed to have spectral characteristics in which a spectral reflectance is about 80% to 100% in a wavelength region of at least 1000 nm to 2500 nm.

Referring to FIG. 3C, light shields 30-1 and 30-2 are positioned inside the dome 21 to prevent light emitted by the light sources 22-1 and 22-2 from directly irradiate the face of the subject to cause scattering of the light irradiating the face. The light source shields 30-1 and 30-2 are provided on both sides of the light sources 22-1 and 22-2, respectively. The embodiment is not limited to the above. The shields maybe provided on only the side of the subject. The shields 30 formed on the inner surface of the doom 21 may be in a shape of an "L", of a crescent, of a semicircle or the like. The shields 30 are located so as not to shield against the image of the subject from the camera 24.

Further, the dome 21 includes a lens shield 31 as illustrated in FIGS. 3A to 3C. The lens shield 31 is shaped like a cylinder. The inner surface of the lens shield 31 is made of a material absorbing light in the near-infrared region. By providing the lens shield 31, stray light can be removed. Exemplary material absorbing the light in the near-infrared region used in the inner surface of the lens shield 31 is, for example, neoprene rubber sponge. However, the material is not limited thereto.

The dome 21 is fixed by a strong magnet, a resin fixing member or the like so as not to move. The light source 22 irradiate the inside of the dome 21 mounted on the base 20. The number of the light sources 22 may be at least one. Referring to FIGS. 2 and 3A-3C, the number of the light sources 22 is one each on the left and right sides of the face, totalling two. The position of the light source may be adjusted to change the position of shade on the face of the subject caused by the irradiation of the light. The installation of the light source 22 inside the dome 21 is described later.

The light sources 22-1 and 22-2 emit the light in the near-infrared region to measure the face. The light sources 22-1 and 22-2 may be a halogen lamp or the like. The halogen lamp is, for example, JD110V50W/P/M manufactured by Iwasaki Electric Co., Ltd. or the like. However, the light source of the embodiment is not limited thereto and may be, for example, a temperature emitting source such as an incandescent lamp and a tungsten halogen lamp, a high pressure discharge lamp (a discharge emission light source) such as a high pressure mercury lamp, a self ballast mercury lamp, a metal halide lamp, and a high pressure sodium lamp, a constant pressure discharge lamp (a discharge emission light source) such as a fluorescence lamp and a low pressure sodium lamp, an electroluminescence light source such as an electroluminescence (EL) and a light emitting diode (LED), and a supercontinuum (SC) light source or the like.

Further, the halogen lamp may be replaced by a double collet type halogen lamp, a PAR lamp, a dichroic mirror or the like. The fluorescent lamp may be replaced by an electric lamp for general lighting, a reflex lamp, a krypton lamp, a mercury lamp, a ballastless (choke-less) mercury lamp, a high pressure sodium lamp, a metal halide lamp, an HQI lamp or the like.

Within the embodiment, it is preferable to use a halogen light source or a LED to capture images in the near-infrared region, for example. The halogen light source and the LED may emit light in the same wavelength region. However, depending on materials of the halogen light source and the LED, the wavelength region of the light may change. Specifically, light spread angles of the halogen light source and the LED are different. The light spread angle of the halogen light source is narrower than that of the LED (light emitted from the halogen light source is more linear than light emitted from the LED). The heat quantity of the light emitted from the LED is smaller than the heat quantity of the light emitted from the halogen light source. Within the embodiment, the selection between the halogen light source and the LED is appropriately determined based on the subject, a purpose of capturing the image, an environment in capturing the image or the like.

For example, a slide member, an arm member or the like may be attached to the light source 22 so that the position of the light source 22 can be freely changed up, down, left or right. The light source 22 maybe freely moved relative to the camera 24 and fixed by a fixing member such as a screw at a desired position. Further, the light source 22 may be moved together with the camera 24 in various directions.

The chin rest 23 is provided to hold and fix the subject at a predetermined position after the subject is inserted into the dome 21. The chin rest 23 can hold the chin of the subject by mounting the chin on a pedestal 32 prepared as illustrated in FIGS. 3A and 3B. The chin rest 23 may have a forehead holding member 33 for holding the forehead of the subject at a predetermined position.

The chin rest 23 has a mechanism of adjusting the height and the left and right position of the pedestal 32. For example, an image captured by the camera 24 or the like is displayed on the screen of the image analysis device 12. The screen may display a scale or the like for enabling adjustments of the height and the left and right position of the pedestal 32. The chin rest 23 has a structure or a movement mechanism for further enabling the lighting device 11 to capture not only a front image of a subject but also a side image and a head hair image when the subject turns the face of the subject obliquely, laterally or backward substantially around a vertical axis.

Referring to FIG. 3A, the periphery of the opening portion 34 receiving the face is covered by an elastic member such as a sponge and cushion in order to prevent external light from intruding via a gap between the face and the opening portion 34. Thus, the light emitted from the light source 22 inside the dome 21 can also prevented from leaking out.

The camera 24 may include a camera 24-1 and a camera 24-2 as an image capturing apparatus. The camera 24-1 maybe a near-infrared camera manufactured by Sumitomo Electric Industries, Ltd., and the camera 24-2 may be a camera for visible light such as D60 with a 60 mm lens. A slide rail 25 as a sliding mechanism is provided so as to mount the cameras 24-1 and 24-2 on a slide rail 25. With this, the cameras can be moved by a slide motion so that the subject can be viewed through the lenses installed in the cameras 24-1 and 24-2. Therefore, within the embodiment, plural cameras may be selected in response to the wavelength regions to be imaged. Further, positions of the cameras 24-1 and 24-2 relative to the dome 21 can be adjusted by a slide mechanism provided in the camera platform 26.

The camera 24-1 obtains an image in a predetermined wavelength region in the near-infrared region. Specifically, the near-infrared camera manufactured by Sumitomo Electric Industries, Ltd which can obtain an image in a wavelength region in about 800 nm to about 2500 nm can be used as the camera 24-1. The lens attached to the camera 24-1 is, for example, a 25 mm lens manufactured by Fujinon Co., Ltd. With the embodiment, a polarizing filter may be provided in order to cancel noise of surface reflection of a facial image of the subject to be captured to thereby obtain a clear image in which glaring on the surface is suppressed. An exemplary polarizing filter is described later.

Further, the camera 24-2 is a camera for visible light. The camera for visible light is used for capturing the image captured by the camera 24-1 before and after capturing the subject by the camera 24-1. The image of the water or the oil captured by the camera 24-1 can be displayed on the image captured by the camera 24-2 by overlapping these images.

Within the embodiment, a band-pass filter is installed in front of the light source or the lens in order to obtain the image in the predetermined wavelength region of the near-infrared region. Within the embodiment, a mechanism of automatically switching the filters by a slide motion may be provided in order to capture images in the plural different wavelength regions of the near-infrared region. The user may manually switch the filters for each time of capturing an image.

The filters of the embodiment includes first filters 35-1 and 35-2 through which light passes from the light sources 22-1 and 22-2 toward the subject, a second filter 36 through which light reflected by the subject passes toward the camera 24 with lens, and a third filter 37 through which the light reflected by the subject passes toward the camera 24 with lens. The first filter 35 may be a UVA cut filter for shielding against UVA or a filter for attenuating near-infrared. The first filter 35 is, for example, GG395 manufactured by SCHOTT AG. For example, the first filter 35 has a thickness of about 3 mm and a size of about 100 mm×100 mm.

Further, the second filter 36 may be a neutral density (ND) filter used so as to overlap the third filter 37 such as a band-pass filter. The ND filter is used to adjust the amount of light introduced into the lens. The types of ND filters are switched depending on the types of the band-pass filter. Referring to FIG. 3B, the second filter 36 and the third filter 37 are mounted on a filter sliding mechanism 38 so that the filters are changed by slide motion in order to capture the images in plural predetermined wavelength regions of the near-infrared region. Thus, types of the second and third filters 36 and 37 and existence or non-existence of the second and third filters 36 and 37 can be easily switched by providing the filter sliding mechanism illustrated in FIG. 3C.

Figure 4:
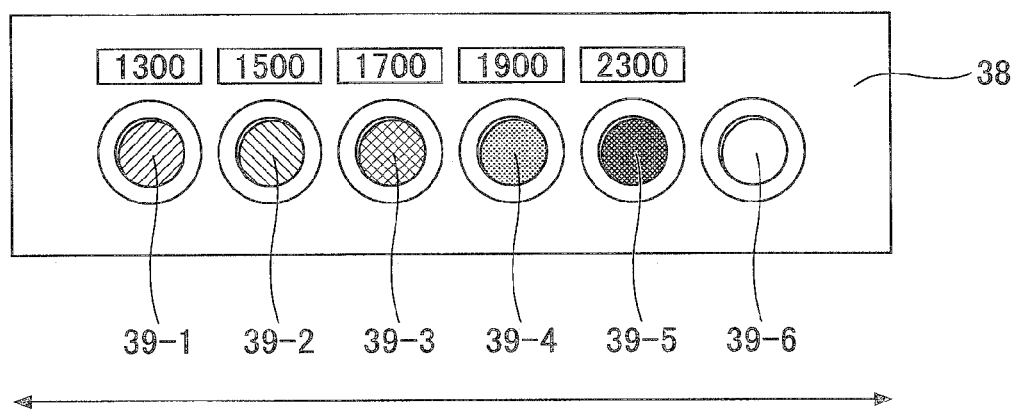
FIG. 4 illustrates sliding motion of filters of the embodiment.

FIG. 4 illustrates sliding motion of the filters of the embodiment. Referring to FIG. 4, the second and third filters 36 and 37 are overlapped and installed in the filter sliding mechanism. The filter sliding mechanism 38 includes five opening portions 39-1 to 39-6. The second and third filters 36 and 37 for capturing images in plural different wavelength regions of the near-infrared region are arranged.

A filter for capturing an image in a wavelength of about 1300 nm is installed in the opening portion 39-1. A filter for capturing an image in a wavelength of about 1460 nm is installed in the opening portion 39-2. A filter for capturing an image in a wavelength of about 1750 nm is installed in the opening portion 39-3. A filter for capturing an image in a wavelength of about 1920 nm is installed in the opening portion 39-4. A filter for capturing an image in a wavelength of about 2300 nm is installed in the opening portion 39-5. Coupled second and third filters 36 and 37 may be installed in the opening portions 39-1 to 39-5, respectively. Instead, filter sliding mechanisms 38 ay be provided respectively for the second filters 36 and the third filters 37.

Nothing is installed in the opening portion 39-6. The opening portion 39-6 may be used in capturing an image without a filter. By moving the filter sliding mechanism 38 right or left in FIG. 4, the filter in front of the lens can be switched. Thus, plural images in the different wavelength regions may be easily obtained using the filters in front of the lens. As described, the slide motion may be automatically performed using a slide control mechanism or the filter sliding mechanism 38 may be manually operated by a user depending on the wavelength regions written in the filter sliding mechanism 38 such as "1300", "1500", "1700", "1900", and "2300" illustrated in FIG. 4.

The types and the number of the filters, the position and the direction of the slide motion in the filter sliding mechanism 38, the amount of the light adjusted by the second filter 36, the position of installing the third filters 37, conditions for band-pass or the like are not limited to the above description. Alternatively, the filter sliding mechanism 38 may be in a circular shape so that the filters are switched by a rotation around a predetermined axis.

Within the embodiment, the images in the predetermined wavelength regions of the near-infrared region are obtained using the plural band-pass filters. Because the amounts of the transmission light differ depending on the predetermined wavelength regions, it is preferable to capture images without changing setup of the camera and the lens in order to prevent repeated readjustments such as focusing of the lens. Therefore, plural band-pass filters (the third filters 37) may be coupled respectively to the ND filters (the second filters 36) so as to be appropriately switched thereby attenuating and adjusting the light amount. The ND filter is, for example, "NG5" manufactured by SCHOTT AG. For example, the ND filter may have a diameter of 25.4 mm and a thickness of 1 mm.

The band-pass filter as the third filter 37 may be a filter manufactured by Spectrogon AB. For example, the band-pass filter as the third filter 37 enables light in a bandwidth region between about 1100 nm and about 1360 nm to pass in order to obtain a basic image. The central wavelength may be about 1300 nm±40 nm.

In order to obtain an image having strong characteristics of absorbing water, it is preferable to obtain an image corresponding to the region A in the line (d) illustrated in FIG. 1. In this case, an image in a wavelength region between about 1300 nm and 1640 nm may be captured. Preferably, an image at a central wavelength of about 1460 nm±45 nm may be captured. In a similar manner, in order to obtain an image having strong characteristics of absorbing water with more sensitivity, it is preferable to obtain an image corresponding to the region B in the line (d) illustrated in FIG. 1. In this case, an image in a wavelength region between about 1860 nm and 2200 nm may be captured. Preferably, an image at a central wavelength of about 1950 nm±56 nm may be captured.

In order to obtain an image having strong characteristics of absorbing oil, it is preferable to obtain an image corresponding to the region C in the line (b) illustrated in FIG. 1. In this case, an image in a wavelength region between about 1700 nm and 1860 nm may be captured. Preferably, an image at a central wavelength of about 1775 nm±50 nm or 1755 nm±20 nm may be captured. In addition, in order to obtain an image having strong characteristics of absorbing oil, it is preferable to obtain an image corresponding to the region D in the line (b) illustrated in FIG. 1. In this case, an image in a wavelength region between about 2230 nm and 2400 nm may be captured. Preferably, an image at a central wavelength of about 2345 nm±50 nm may be captured. Since there are plural peaks in the region D, one of the wavelengths in the region may be selected or two or more wavelengths may be selected in order to capture images. Since characteristics of absorbing water have great variation in the wavelength region between about 2230 nm and 2400 nm as in (a) of FIG. 1, an image is captured in an appropriate wavelength region depending on conditions in the subject such as drying and humidity.

The filter used to capture the images in the wavelength regions of the near-infrared region may be realized by one filter or plural filters.

Further, within the embodiment, the color chart 40 may be installed in front of the pedestal 32 on the side of the camera 24 so that the color chart 40 faces the camera 24. With this, the facial image of a subject and the color chart 40 are captured by the camera 24 in an image. Thus, it is becomes possible to correct plural images using the color chart 40 in order to improve an accuracy of analysis. Examples of the color chart are described later.

The facial images of the subject captured by the camera 24 using the above lighting device 11 are output to the image analysis device 12 via the cable 13 illustrated in FIG. 1. For example, the communication between the lighting device 11 and the image analysis device 12 maybe wireless communication using infrared rays or wired communication via a LAN cable. Further, an image may be transmitted to the image analysis device 12 located in a distant place.

Within the embodiment, the images may be captured before, immediately after, after, or a predetermined time after coating with an external dermatological medication such as lotion and emulsion.

Within the embodiment, the image captured by the lighting device 11 may be captured upon a request from a user or real time images continuously captured. Further, the image captured by the lighting device 11 may include the skin of the face of the subject such as a cheek and forehead, the eyelids, the eyes, under the eyes, the eye areas, the nose, the mouth, the mouth area, lip ends, the ears, the eyebrows, the chin, the neck, the head hair, the arms, the hands, the legs and so on. The content analyzed by the image analysis device 12 may correspond to all images captured by the above lighting device 11.

Next, an example of the polarizing filter of the embodiment is described. Unwanted reflection light such as glare caused by the light source may exist on the surface of the subject. The unwanted reflection light influences on luminance of the captured image thereby causing error in quantitative evaluation by analyzing the images.

Then, a polarizing filter may be installed before, after or before and after the lense of the camera 24-1 and/or 24-2. The polarizing filter may be installed before the light source instead of in the vicinity of the lenses. Further, within the embodiment, the polarizing filter may be installed in both of the lens and the light source. The number of the polarizing filter is one or plural.

With this, the unwanted reflection light unnecessary for the analysis can be removed. Within the embodiment, noise can be removed by installing the filter and the analysis becomes highly accurate.

Next, an example of the color chart 40 of the above embodiment is described. Ordinarily, when the images are compared using quantitative evaluation by the image analysis, there may occur a slight difference depending on conditions for capturing the images. Therefore, within the embodiment, an arbitrary color chart 40 used for specifying a reflection coefficient is used to correct the luminance value of the captured image to enable accurate analysis by comparing between the images regardless of times when the images are obtained.

Figure 5A:
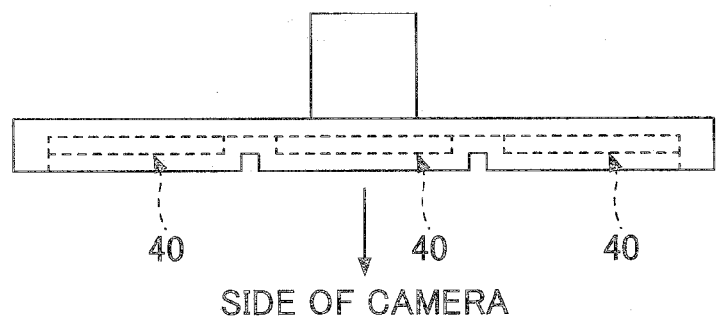
FIG. 5A illustrates an exemplary color chart installed in the lighting device of the embodiment.
Figure 5B:
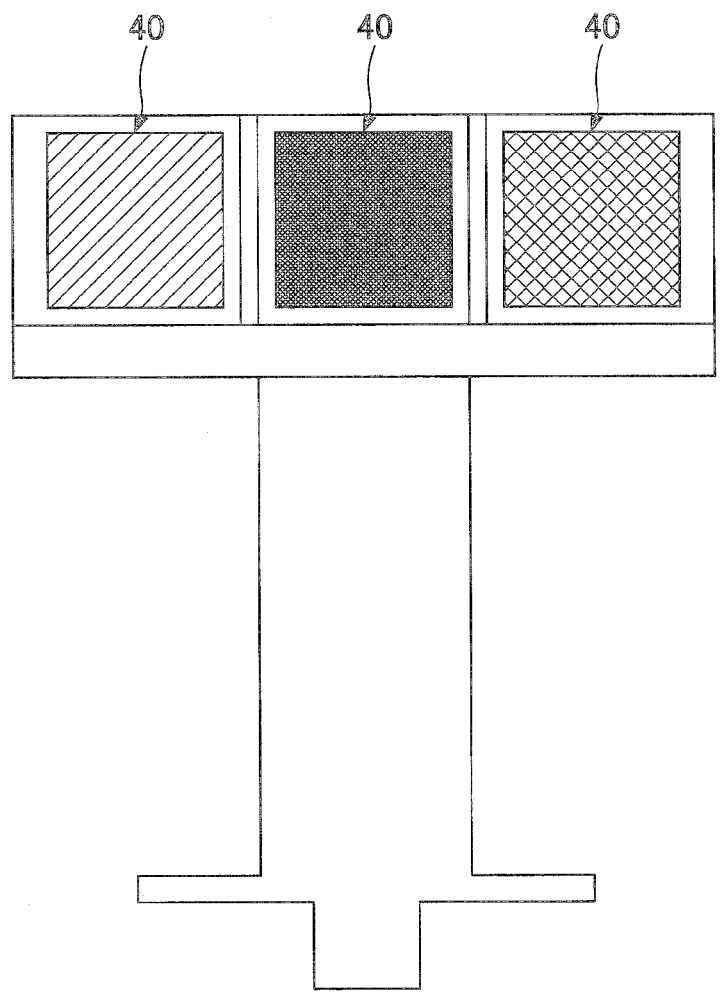
FIG. 5B illustrates an exemplary color chart installed in the lighting device of the embodiment.

The color chart 40 installed in the lighting device 11 is described next. FIG. 5A and FIG. 5B illustrate an exemplary color chart installed in the lighting device of the embodiment. FIG. 5A is a plan view of a color chart board in which the color charts are arranged. FIG. 5B is a front view of the color chart board viewed from the camera 24.

Referring to FIG. 5A and FIG. 5B, the three color charts 40 having different reflection coefficients are arranged in parallel on the color chart board. The color charts 40 illustrated in FIGS. 5A and 5B may be selected depending on the wavelength of the light source used for capturing images of a subject. By using the color charts 40 as described above, it is possible to correct the luminance of the images to be captured.

The color charts 40 illustrated in FIGS. 5A and 5B may be located at a position where the image of the color chart is captured together with the subject. Within the embodiment, the color chart 40 may be mounted in front of the pedestal 32 so that the color charts 40 face the camera 24. Specifically, referring to FIGS. 5A and 5B, a lower potion of the color chart board is inserted into a recess formed on a side of the chin rest 23 of the lighting device 11. With this, the color charts 40 can be easily attached to or detached from the lighting device 11. When necessary, the color charts 40 may be switched depending on the performance or the accuracy of the camera 24, the type and the wavelength of the light source.

The number, the size, the shape, the luminance and the arrangement of the color charts 44 are not limited to those described in FIGS. 5A and 5B. It is sufficient to provide at least one color chart.

Next, an example of the image analysis device 12 is described.

Figure 6:
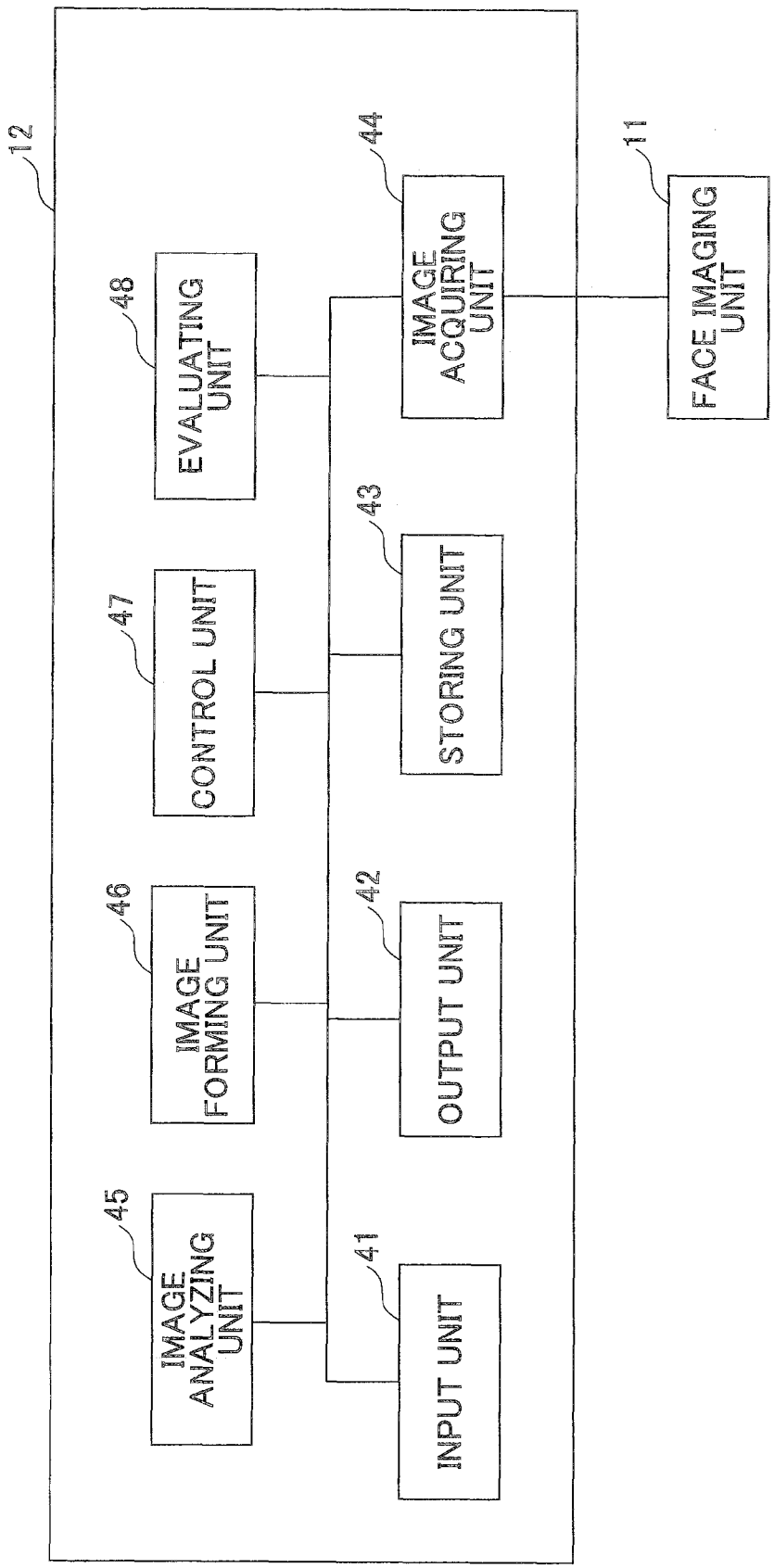
FIG. 6 illustrates an exemplary function structure of a picture quality controlling device of an embodiment.

FIG. 6 illustrates an exemplary functional structure of the image analysis device of the embodiment. Referring to FIG. 6, the image analysis device 12 includes an input unit 41, an output unit 42, a storing unit 43, an image acquiring unit 44, an image analyzing unit 45, an image forming unit 46, a control unit 47, and an evaluating unit 48.

The input unit 41 receives various instructions from a user to start or end an image obtention instruction, an image analysis instruction, and an evaluation instruction or the like. The input unit 41 includes a keyboard and a pointing device such as a mouse, for example. The input unit 11 has a function of inputting an image including a part of a subject captured by an image capturing unit 24 such as a digital camera.

The output unit 42 displays or outputs a content input by the input unit 41 or a content performed based on the content input by the input unit 41. The output unit 42 includes a display, a speaker or the like. Further, the output unit 42 may have functions as a printer or the like. In this case, a result of image analysis may be printed on a print medium such as paper so as to be provided to a user, the subject or the like.

The input device 41 and the output device 42 may be an integrated input and output unit such as a touch panel. In this case, a user's finger, a pen-type input device, or the like maybe used to touch the touch panel.

The storing unit 43 stores various data of image information such as captured images acquired by the image acquiring unit 44, a result of analyzing the images by the image analyzing unit 45, and an evaluation result generated by the image forming unit 46. The storing unit 43 can read out the stored various data when necessary.

The image acquiring unit 44 acquires facial images of the subject captured by the camera 24 using the lighting device 11. The image acquiring unit 44 can set the type, the position and the number of the light sources 22 in the lighting device 11 depending on a content of the images to be captured. Further, the image acquiring unit 44 generates instruction information indicative of image capturing conditions in order to acquire images filtered by the predetermined band-pass filter to be in a predetermined wavelength region of the near-infrared region. Here, the above first to third filters 35 to 37 are combined and used in the camera 24 in the lighting device 11. The image acquired by the image acquiring unit 44 is stored in the storing unit 43.

The image analyzing unit 45 corrects luminance of the images acquired by the image acquiring unit 44, calculates an average luminance value of the images acquired by the image acquiring unit 44, analyzes luminance transitions during coating of an external dermatological medication such as lotion and emulsion, calculation of the luminance transition value, setup of pseudo-colors corresponding to areas selected by the user, or the like. The image analyzing unit 45 can analyze a skin or the like using the images before, immediately after, or after coating with an external dermatological medication, and can evaluated the result of the analysis. The image analyzing unit 45 may analyze or evaluate an entire skin of the captured facial images or only a part of the entire skin designated by the user or the like. The number of the designated areas may be one or plural.

Further, within the embodiment, the image captured by the image analyzing unit 45 maybe analyzed in real time while acquiring the images from the lighting device 11 or while reading the stored images previously stored in the storing unit 43.

The images analyzed by the image analyzing unit 45 may be images of skins such as a cheek, a forehead, an arm, a hand, or a leg. Further, the image analyzing unit may analyze head hair. An example of processing in the image analyzing unit 45 is described later.

The image forming unit 46 generates an image to be presented to a user base on the result obtained by analyzing with the image analyzing unit 47. Specifically, the image forming unit 46 synthesizes pseudo-colors corresponding to luminance differences analyzed by the image analyzing unit 45. Then, the synthesized images are displayed on a screen of the image analysis device 12.

The image forming unit 46 can display the image after modifying the image so that the synthetic image is easily viewed by the user. For this, before the synthetic image is displayed on a screen, the luminance area may be enlarged for a predetermined area, a differential image may be calculated, or the luminance may be inversed.

The image forming unit 46 generates the pseudo-colors corresponding to the areas designated by the user in the image. Specific processes in the image forming unit 46 are described later.

Further, the control unit 47 controls entire components of the image analysis device 12. Specifically, the control unit 47 controls an image analysis process, an image generation process or the like based on an instruction or the like from the input unit 41 by the user or the like, for example.

An execution program (an image analysis program) for causing a computer to execute various functions is generated for the above image analysis device 12. After installing the execution program on, for example, a general purpose computer or a server, the image analysis device 12 is realized. Then, the images in the predetermined wavelength region of the near-infrared region captured before and after coating with the external dermatological medication and the predetermined time after coating with the external dermatological medication can be analyzed by the image analysis device 12.

The hardware structure of the computer by which the image analysis process is realized in the embodiment is described with reference to the figures.

Figure 7:
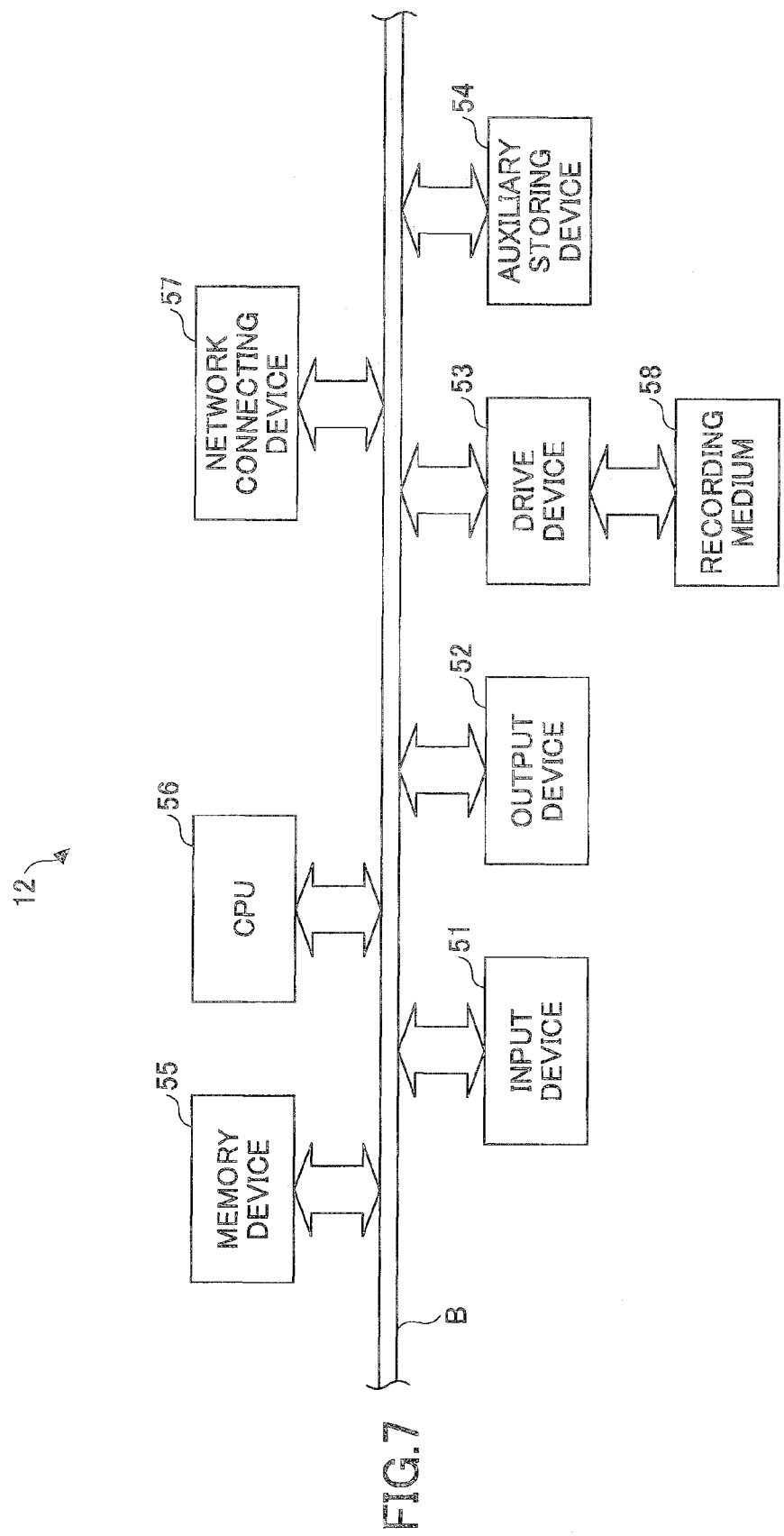
FIG. 7 illustrates an example hardware structure enabling an image analyzing process of the embodiment.

FIG. 7 illustrates an example hardware structure enabling the image analysis process of the embodiment. The image analysis device realized by the computer illustrated in FIG. 7 includes an input device 51, an output device 52, a drive device 53, an auxiliary storing device 54, a memory device 55, a Central Processing Unit (CPU) 56 performing various controls, and a network connecting device 57. These are mutually connected via a system bus B.

The input device 51 is provided for a user or the like to run programs and input various operation signals, and includes a keyboard, a pointing device such as a mouse or the like. Various data such as the facial images of the subject imaged at the measured and evaluated portions after coating with the external dermatological medication or after irradiating the faces with the near-infrared are obtained from an external device connected to the network connecting device 57 via a communication network and further through the input device 51.

The output device 52 includes a display for displaying various windows, data or the like necessary for operating the computer which carries out processes of the embodiment of the present invention. The output device 52 can display an execution transit, a result, or the like of the program with a control program installed in the CPU 56. The output device 52 can print the above result on the print medium such as paper so as to be presented to the user or the like.

In the embodiment of the present invention, the execution program installed on the computer may be provided by a portable recording medium 58 such as a Universal Serial Bus (USB) and a CD-ROM. The recording medium 58 having the execution program recorded on it may be installed in the drive device 53. The execution program included in the recording medium 58 is installed on the auxiliary storing device 54 via the drive device 53 from the recording medium 58.

The auxiliary storing device 54 is a storage means such as a hard disk. The auxiliary storing device 44 can store the execution program of the embodiment, and the control program installed on the computer, and so on, thereby enabling to input or output the execution programs, the control programs, and so on when necessary.

The memory device 55 stores the execution program which is read out of the auxiliary storing device 54 by the CPU 56, and so on. The memory device 55 includes a Read-Only Memory (ROM), a Random Access Memory (RAM) or the like.

The CPU 56 controls entire processes of the computer such as various calculations and inputs and outputs of data to and from various portions in a hardware configuration in order to realize various processes for the analysis and the evaluation with the control program such as an operating system (OS) and the execution program stored in the memory device 55. The various information or the like necessary for running the program may be obtained from the auxiliary storing device 54. The results of the execution may be stored in the auxiliary storing device 44.

When the network connecting device 57 is connected to a communication network or the like, the network connecting device 57 may obtain the execution program from another terminal connected to the communication network, or provide execution results obtained by carrying out the execution program or the execution program itself of the embodiment to another terminal and so on.

The network connecting device 57 can obtain various data of the skin images which are captured after coating with the external dermatological medication or after irradiating with ultraviolet rays at an evaluation portion and already measured by the external device connected to the communication network.

With the above-mentioned hardware configuration, the image analysis processes of the embodiment can be carried out. Further, the image analysis process of the embodiment can be easily realized by installing the program in the general purpose computer and so on.

Figure 8:
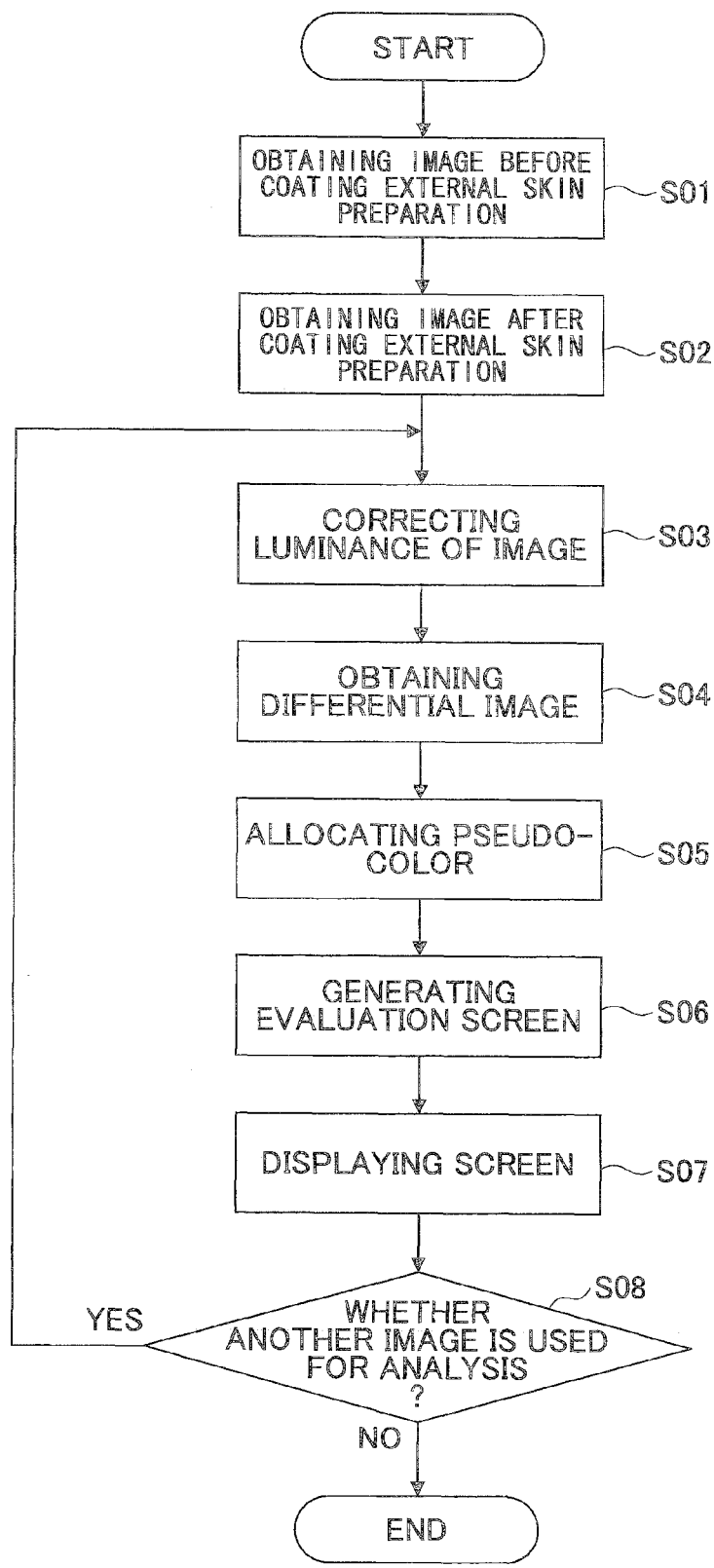
FIG. 8 illustrates an exemplary flowchart illustrating the image analyzing process of the embodiment.

Next, the image analysis process of the embodiment is described. FIG. 8 is a flowchart of an example image analysis process of the embodiment.

Referring to FIG. 8, the image analysis process obtains a facial image of a subject before coating with an external dermatological medication as a base image in step S01. Then, a facial image of the subject after coating with the external dermatological medication is obtained. In steps S01 and S02, the facial images are captured in use of a light source such as a halogen lamp in the above lighting device or the like and captured in a predetermined wavelength region of the near-infrared region filtered by the above filters.

The base image maybe previously formed and stored in the storing unit 43 instead of obtaining in step S01.

Further, after coating with the external dermatological medication, it is preferable to let a predetermined time elapse so as to allow the effects of the coating to set before obtaining the facial image in step S02. The elapse time differs depending on the external dermatological medication, the amount of coating with the external dermatological medication, and a portion where the external dermatological medication is coated. Therefore, the image obtained in step S02 may be an image immediately after coating with the dermatological medication, or the image immediately after coating and an image of a predetermined time (e.g., 10 or 30 minute) after coating which are continuously obtained. Further, plural images at predetermined times after coating may be continuously obtained. The images obtained in step S02 are compared with the image obtained in step S01 in a later step.

Next, the luminance of images obtained in steps S01 and S02 are corrected in step S03. A differential image between the two images is generated in step S04. The processes in steps S03 and S04 may be performed for an entire image or an area or plural areas in the images which are previously set by the user.

In step S04, predetermined pseudo-colors are allocated to the differential image obtained in step S04 depending on a difference value of the luminance for each predetermined pixel in step S05. Further, the allocated pseudo-colors are synthesized with the differential image to thereby generate an evaluation image or the like in step S06. Then, the evaluation image is displayed on the screen of the image analysis device 12 in step S07. In step S06, the evaluation image or the like is generated using the result of the analysis obtained by the image analyzing unit 45 and the evaluation result obtained in the evaluating unit 48 or the like.

It is determined whether the analysis is performed using another image in step S08. If another image is analyzed in YES of step S08, the process returns to step S03. Then, the other image obtained in step S02 is used to perform the following process to thereby analyze or evaluate the other image.

When the other image is analyzed, the predetermined pseudo-color may be used as an index as described above. The index may be predetermined or may be arbitrarily set based on the evaluation portion on the image, the ingredients of the external dermatological medication, a content of the index already introduced or the like. With this, it is possible to easily and quickly evaluate the skin conditions such as uneven coating after coating with the external dermatological medication on the user.

Next, an example of the image obtention and the image analysis of the embodiment is described.

An exemplary image obtained by the lighting device 11 is described in comparison with an image captured by a conventional lighting device.

Figure 9:
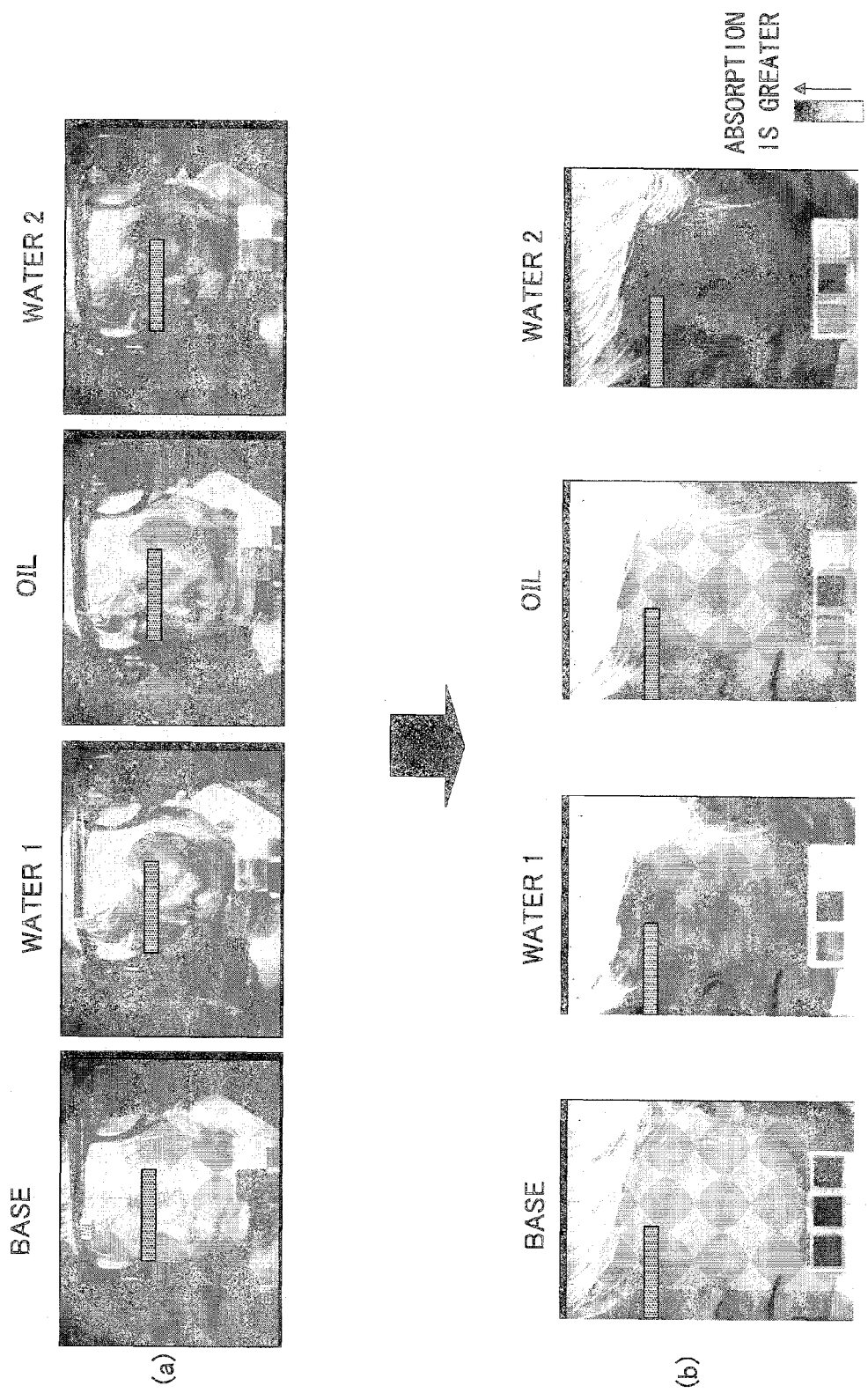
FIG. 9 illustrates exemplary images captured by a conventional lighting device and exemplary images captured by the lighting device of the embodiment.

FIG. 9 illustrates exemplary images captured by the conventional lighting device and exemplary images captured by the lighting device of the embodiment. In FIG. 9, (a) corresponds to the exemplary images of "base", "water 1", "oil", and "water 2" captured by the conventional lighting device, and (b) corresponds to the exemplary images of "base", "water 1", "oil", and "water 2" captured by the lighting device of the embodiment.

Here, the "base" is an image captured at a central wavelength of about 1300 nm±40 nm. The "water 1" is an image captured at a central wavelength of about 1500 nm±45 nm. The "oil" is an image captured at a central wavelength of about 1775 nm±50 nm. The "water 2" is an image captured at a central wavelength of about 1920 nm±55 nm.

In the conventional lighting device in (a) of FIG. 9, cheekbones and eyelids in "base", "water1", "oil", and "water2" is whitened or shows halation. Meanwhile, referring to (b) of FIG. 9, images according to the embodiment accurate enough to show no shine.

The image of the "oil" at the central wavelength may be similar to an image of the "oil" in a wavelength region between about 2230 nm to about 2400 nm (preferably at a central wavelength of 2345 nm±50 nm). Hereinafter, the image of "oil" has a property similar to the above.

Next, an example of an analysis image is described next. The following three examples are explained: (1) a left cheek is coated with lotion using cotton, and the coated left cheek is analyzed before and immediately after coating; (2) the left cheek with cotton is coated with emulsion using cotton, and the coated left cheek is analyzed before, immediately after, and 10 minutes after coating; and (3) hair treatment is sprayed onto left head hair, and the sprayed left head hair is analyzed before, and immediately after coating.

Figure 10:
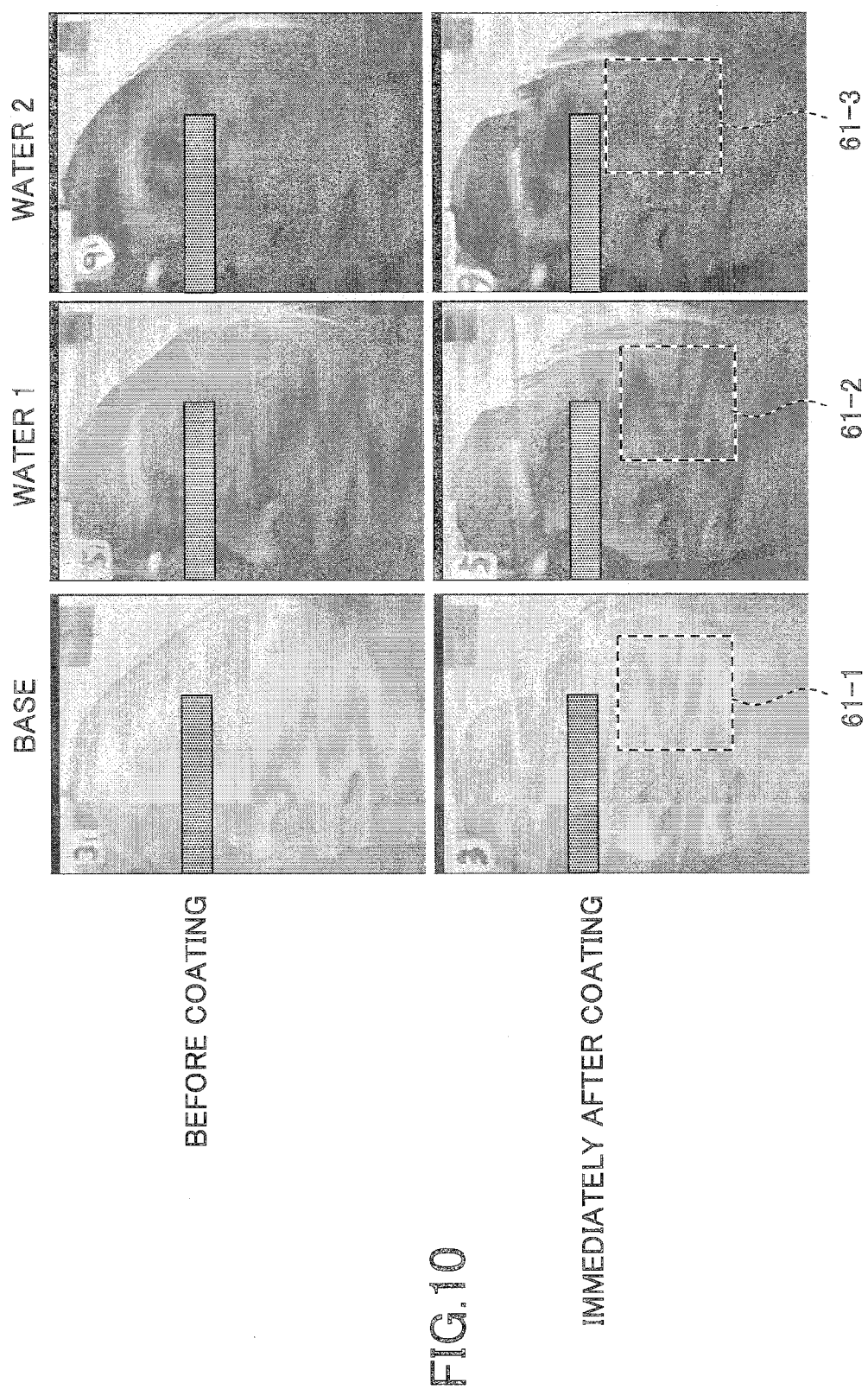
FIG. 10 illustrates exemplary skin images before and after coating with lotion.

FIG. 10 illustrates exemplary skin images before and after coating with the lotion. Referring to FIG. 10, the images of "base", "water1", and "water2" before and after coating are illustrated. Referring to FIG. 10, the lotion as an external dermatological medication is applied to areas 61-1 to 61-3, and images are captured immediately after coating.

Luminance of the images illustrated in FIG. 10 are corrected. The luminance is corrected by calculating an average value in a predetermined pixel unit (e.g., 20 pixels×20 pixels) inside the image and correcting the entire image using two references, i.e., luminance of 30 for black and luminance of 120 for gray. With this, the noise on the images can be reduced and the images are smoothed.

Referring to FIG. 10, existence of water makes the image dark. Especially, the area 61-3 on the image of "water2" in the near-infrared region is darkened after coating with the lotion.

Next, an example of specific analysis in the embodiment when external dermatological medications (lotion or emulsion) are used for coating a subject is explained.

Figure 11:
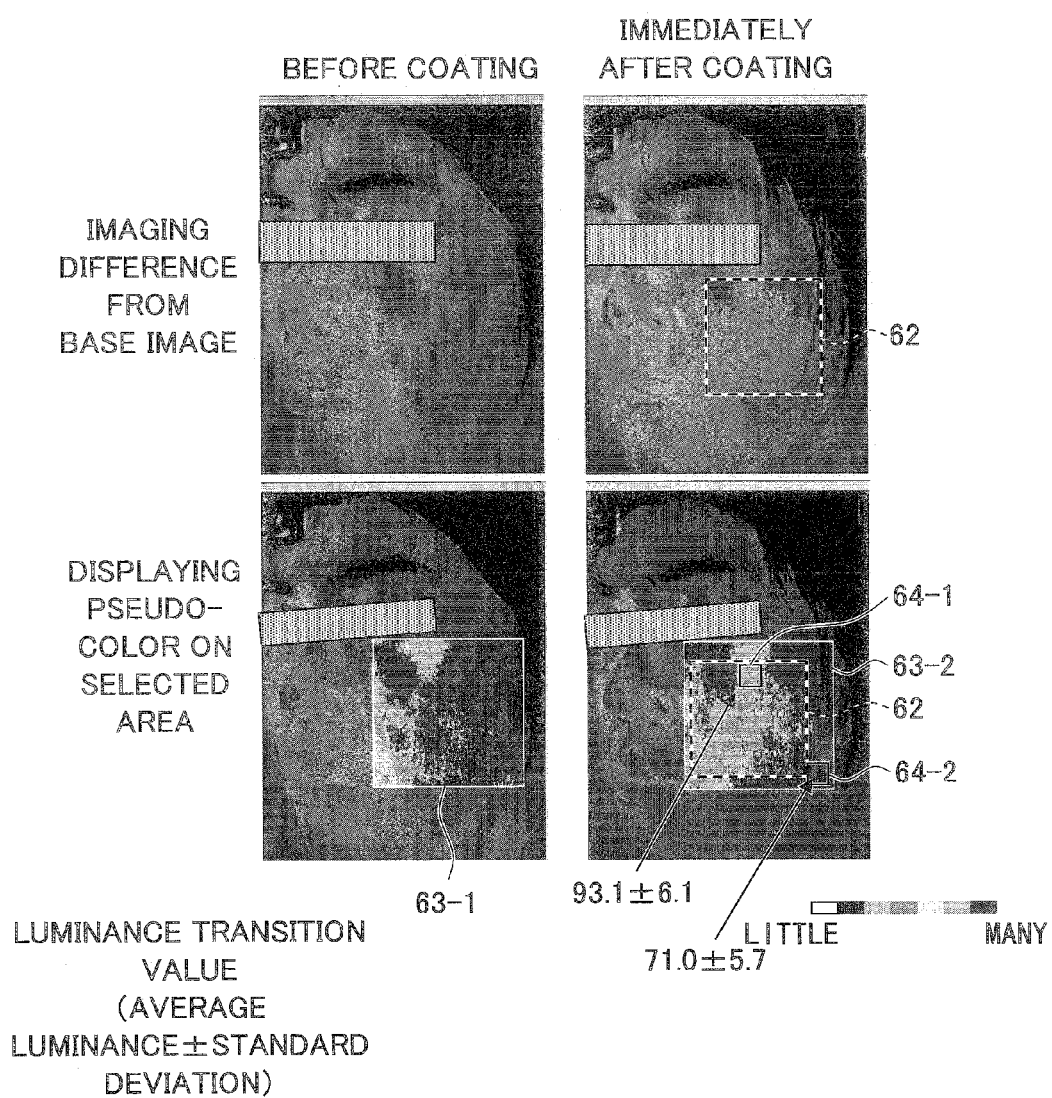
FIG. 11 illustrates luminance transitions before and after coating with lotion in "water 1".

FIG. 11 illustrates luminance transitions before and after coating with lotion in "water 1". FIG. 11 illustrates images obtained by imaging differences from the base image before and immediately after coating with the lotion, and images with pseudo-colors inside selected areas for emphasizing the differences. Further, referring to FIG. 11, differential images are calculated by subtracting the base image from an image of "water1" after correcting luminance in order to correct reflection on the skin surface to a certain extent. In this image, a portion coated with water is whitened.

Referring to FIG. 11, the coated area is coated with lotion. The user selects a predetermined selected area using the input unit 41 such as a mouse (dragging the mouse). Pseudo-colors are set in the selected area by the image analyzing unit. Then, a result is displayed by the image forming unit 46.

Within the embodiment, the pseudo-colors are provided to display predetermined colors or patterns corresponding to luminance differences. Said differently, depending on the values of the luminance transitions, pseudo-colors are displayed. The displayed pseudo-colors are synthesized with the facial image by overlapping the facial image. Therefore, it is possible to accurately know the location of and the level of the luminance differences.

Referring to FIG. 11, when the pseudo-color display on the selected area 63-1 before coating is compared with the pseudo-color display on the selected area 63-2 immediately after coating, the amount of the luminance transitions is greater in the selected area 63-2 than in the selected area 63-1. Meanwhile, the image analyzing unit 45 may allocate the pseudo-colors corresponding to predetermined values of the luminance transition for each predetermined pixel unit such as squared pixels (e.g., 1×1, 2×2).

Further, referring to FIG. 11, the image analyzing unit 45 obtains the value of the luminance transition. Referring to FIG. 11, in luminance transition measuring areas 64-1 and 64-2 set using the input unit 41 by the user. The value of the luminance transition such as "average luminance±standard deviation" is displayed for the set luminance transition measuring areas 64-1 and 64-2. The number of the luminance transition measuring area may be one.

Referring to FIG. 11, the value of the luminance transition in the luminance transition measuring area 64-1 may be 93.1±6.1 and the value of the luminance transition in the luminance transition measuring area 64-2 may be 71.0±5.7.

Figure 12:
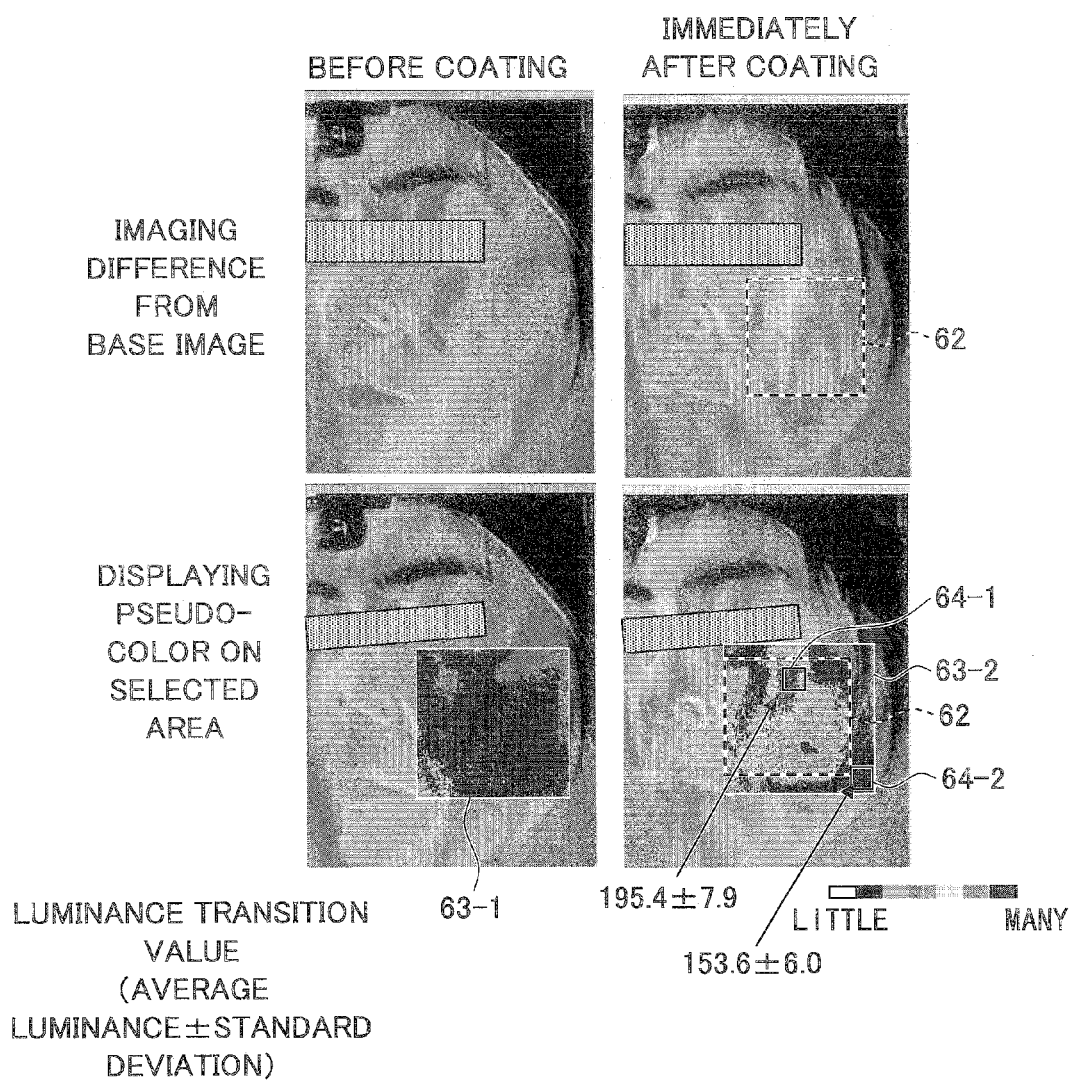
FIG. 12 illustrates luminance transitions before and after coating with lotion in "water 2".

FIG. 12 illustrates luminance transitions before and after coating lotion in "water 2". FIG. 12 illustrates images obtained by imaging differences from the base image before and immediately after coating with the lotion, and images with pseudo-colors inside selected areas for emphasizing the differences. Further, referring to FIG. 12, differential images are calculated by subtracting the base image from an image of "water2" after correcting luminance in order to correct reflection on the skin surface to a certain extent. In this image, a portion coated with water is whitened.

Referring to FIG. 12, the coated area is coated with lotion. The user selects predetermined selected areas 63-1 and 63-2 using the input unit 41 such as a mouse (dragging the mouse). Pseudo-colors are set in the selected area by the image analyzing unit 45. Then, a result is displayed by the image forming unit 46.

Referring to FIG. 12, when the pseudo-color display on the selected area 63-1 before coating is compared with the pseudo-color display on the selected area 63-2 immediately after coating, the amount of the luminance transitions is greater in the selected area 63-2 than in the selected area 63-1.

Further, referring to FIG. 12, the image analyzing unit 45 sets the luminance transition measuring areas 64-1 and 64-2. The value of the luminance transition such as "average luminance±standard deviation" may be displayed for the set luminance transition measuring areas 64-1 and 64-2. Referring to FIG. 12, the value of the luminance transition in the luminance transition measuring area 64-1 may be 195.4±7.9 and the value of the luminance transition in the luminance transition measuring area 64-2 may be 153.6±6.0. It is known that the luminance difference is greater in "water2" than in "water1".

The luminance transitions of water in the selected areas before and after coating with the lotion are calculated after performing several processes. Depending on the values of the luminance transitions, pseudo-colors are displayed. The displayed pseudo-colors are synthesized with the facial image by overlapping the facial image. The luminance values of "water1" and "water2" greatly change on portions where the lotion is applied. However, transition patterns in "water1" and "water2" are slightly different. This is because detection sensitivities of water differ relative to the wavelengths or depths inside the skin, from which the water is detected, differ relative to the wavelengths. Vide M. Egawa, H. Arimoto, T. Hirao, M. Takahashi, and Y. Ozaki, Regional Difference of Water Content in Human Skin Studied by Diffuse-reflectance Near-infrared Spectroscopy-Consideration of Measurement Depth-, Appl Spectrosc, 60 (1), 24-28(2006).

Figure 13:
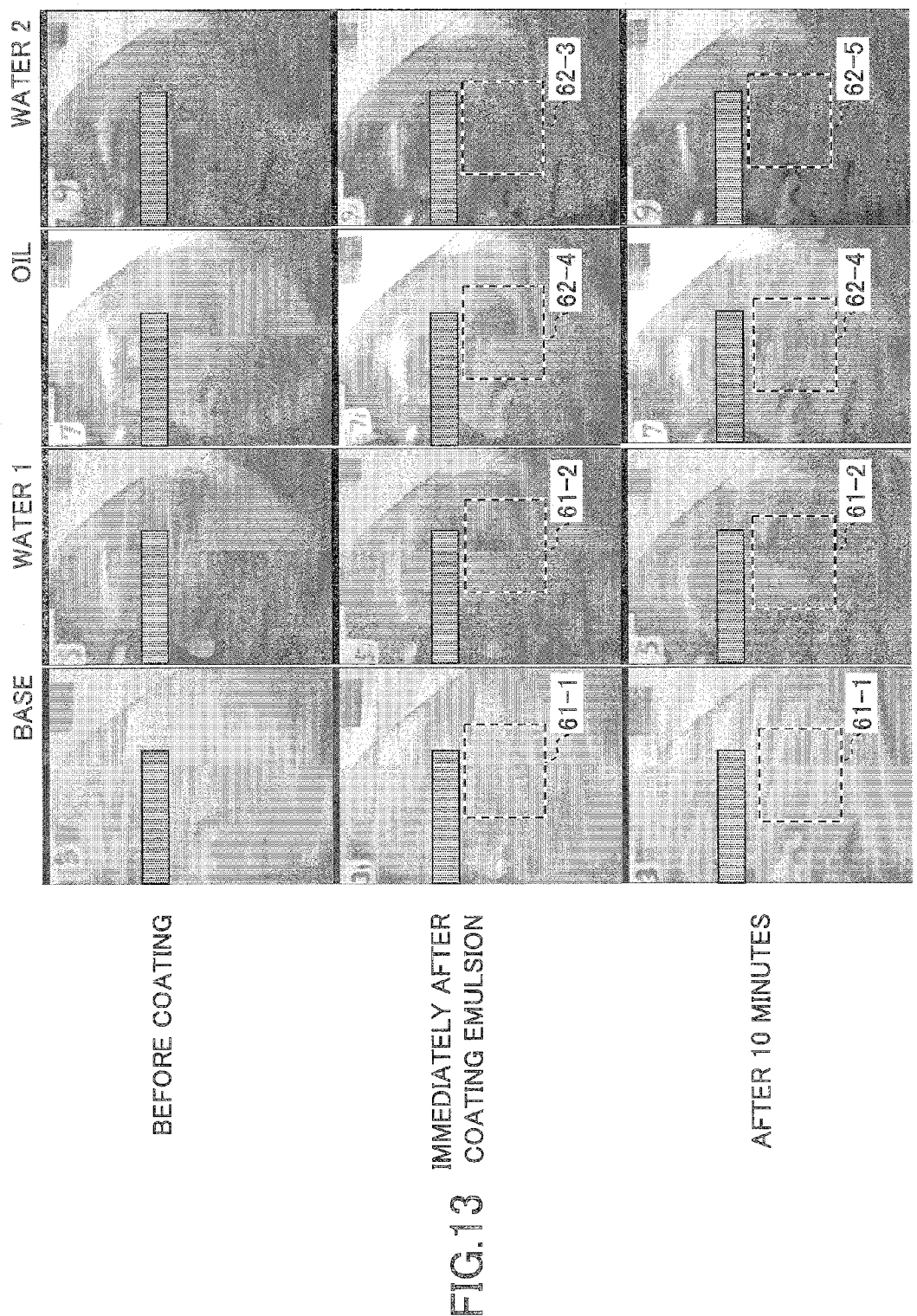
FIG. 13 illustrates exemplary skin images before and after coating with emulsion.

Next, skin images before and after coating with emulsion are described. FIG. 13 illustrates exemplary skin images before and after coating with the emulsion. Referring to FIG. 13, the images of "base", "water1", "oil", and "water2" before, immediately after, and 10 minutes after coating are illustrated.

Here, the "base" is an image captured at a central wavelength of about 1300 nm±40 nm. The "water 1" is an image captured at a central wavelength of about 1500 nm±45 nm. The "oil" is an image captured at a central wavelength of about 1775 nm±50 nm. The "water 2" is an image captured at a central wavelength of about 1920 nm±55 nm. Referring to FIG. 13, the lotion as an external dermatological medication is applied on areas 61-1 to 61-4, and images are captured immediately after coating. The above luminance correction is applied to all images obtained above.

Referring to FIG. 13, the areas 62-1 to 62-4 correspond to coated areas of "base", "water1", "oil", and "water2", respectively. When water or oil exists in a portion of the image, such portion is blackened (darkened) as in the coated areas 62-1 to 62-4. Since the emulsion is applied, the coated areas on the images of oil and water are blackened. The coated area becomes less black 10 minutes after coating in comparison with the blackness immediately after coating.

Figure 14:
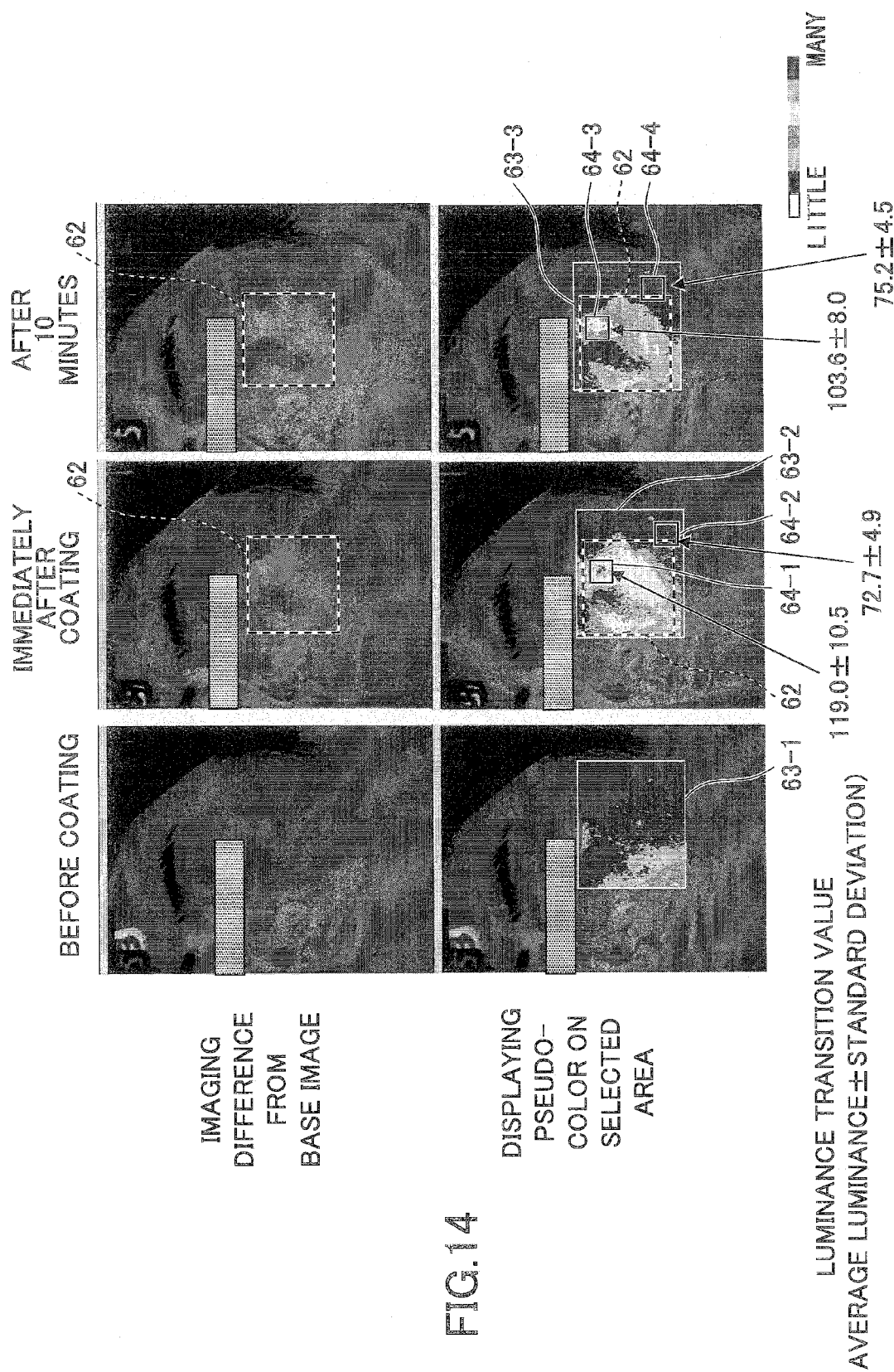
FIG. 14 illustrates luminance transitions before and after coating with emulsion in "water 1".

FIG. 14 illustrates luminance transitions before and after coating emulsion in "water 1". FIG. 14 illustrates images obtained by imaging differences from the base image before and immediately after coating, and images with pseudo-colors inside selected areas for emphasizing the differences. Further, referring to FIG. 14, differential images are calculated by subtracting the base image from the image of "water1" after correcting luminance in order to correct reflection on the skin surface to a certain extent. In this image, a portion coated with water is whitened.

Referring to FIG. 14, the coated area 62 is further coated with lotion. The user selects predetermined selected areas 63 using the input unit 41 such as a mouse (dragging the mouse). Pseudo-colors are set in the selected areas 63 by the image analyzing unit 45. Then, a result is displayed by the image forming unit 46.

Within the embodiment, the pseudo-colors are provided to display predetermined colors or patterns corresponding to the luminance differences. Said differently, depending on the values of the luminance transitions, pseudo-colors are displayed. The displayed pseudo-colors are synthesized with the facial image by overlapping the facial image. Therefore, it is possible to accurately know the location of and the level of the luminance differences.

Referring to FIG. 14, when the pseudo-color display on the selected area 63-1 before coating is compared with the pseudo-color display on the selected area 63-2 immediately after coating, the amount of the luminance transitions is greater in the selected area 63-2 than in the selected area 63-1. Further, when the pseudo-color display on the selected area 63-2 immediately after coating is compared with the pseudo-color display on the selected area 63-3 10 minutes after coating, the amount of the luminance transitions is smaller in the selected area 63-3 than in the selected area 63-2.

The differential image is obtained by subtracting the base image from the images of water or oil undergoing luminance correction. In the differential image, portions coated with water or oil are whitened. Because the emulsion is applied, the image "water1" is maintained after 10 minutes. This means that the emulsion remains on the skin.

When luminance transitions in the selected areas before and after coating with the lotion are calculated after performing several processes as in the above lotion, the value of the luminance transitions immediately after coating is 119.0±10.5 and the value of the luminance transitions on a luminance transition measuring area 64-2 is 72.7±4.9. Further, the value of the luminance transitions in the luminance transition measuring area 64-3 10 minutes after coating is 103.1±8.0 and the value of the luminance transitions in the luminance transition measuring area 64-4 may be 75.2±4.5.

Figure 15:
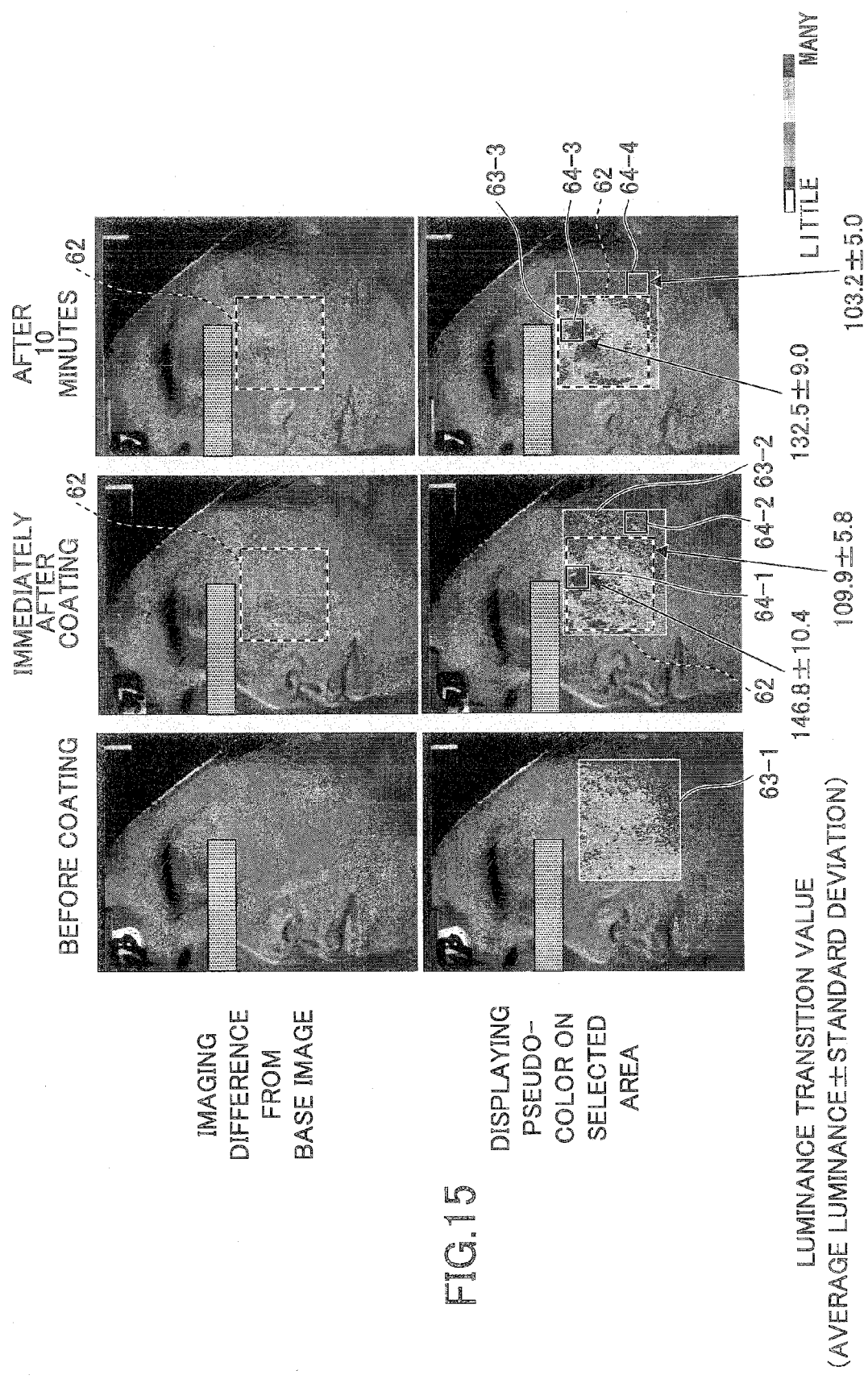
FIG. 15 illustrates luminance transitions before and after coating with emulsion in "oil".

FIG. 15 illustrates luminance transitions before and after coating the emulsion in "oil". FIG. 15 illustrates images obtained by imaging differences from the base image before, immediately after, and 10 minutes after coating, and images with pseudo-colors inside selected areas for emphasizing the differences. Further, referring to FIG. 15, differential images are calculated by subtracting the base image from an image of "oil" after correcting luminance in order to correct reflection on the skin surface to a certain extent. In this image, a portion coated with oil is whitened.

Referring to FIG. 15, the coated area 62 is further coated with lotion. The user selects predetermined selected areas 63 using the input unit 41 such as a mouse (dragging the mouse). Pseudo-colors are set in the selected areas 63 by the image analyzing unit 45. Then, a result is displayed by the image forming unit 46.

Within the embodiment, the pseudo-colors are provided to display predetermined colors or patterns corresponding to the luminance differences. Said differently, depending on the values of the luminance transitions, pseudo-colors are displayed. The displayed pseudo-colors are synthesized with the facial image by overlapping the facial image. Therefore, it is possible to accurately know the location of and the level of the luminance differences.

Referring to FIG. 15, when the pseudo-color display on the selected area 63-1 before coating is compared with the pseudo-color display on the selected area 63-2 immediately after coating, the amount of the luminance transitions is greater in the selected area 63-2 than in the selected area 63-1. Further, when the pseudo-color display on the selected area 63-2 immediately after coating is compared with the pseudo-color display on the selected area 63-3 10 minutes after coating, the amount of the luminance transitions is smaller in the selected area 63-3 than in the selected area 63-2.

The differential image is obtained by subtracting the base image from the images of water or oil undergoing luminance correction. In the differential image, portions coated with water or oil are whitened. Because the emulsion is applied, the image "oil" is maintained after 10 minutes. This means that the emulsion remains on the skin.

When luminance transitions in the selected areas before and after coating with the lotion are calculated after performing several processes as in the above lotion, the value of the luminance transitions immediately after coating is 146.0±10.4 and the value of the luminance transitions on the luminance transition measuring area 64-2 is 109.9±5.8. Further, the value of the luminance transitions in the luminance transition measuring area 64-3 10 minutes after coating is 132.5±5.8 and the value of the luminance transitions in the luminance transition measuring area 64-4 may be 103.2±5.0.

Figure 16:
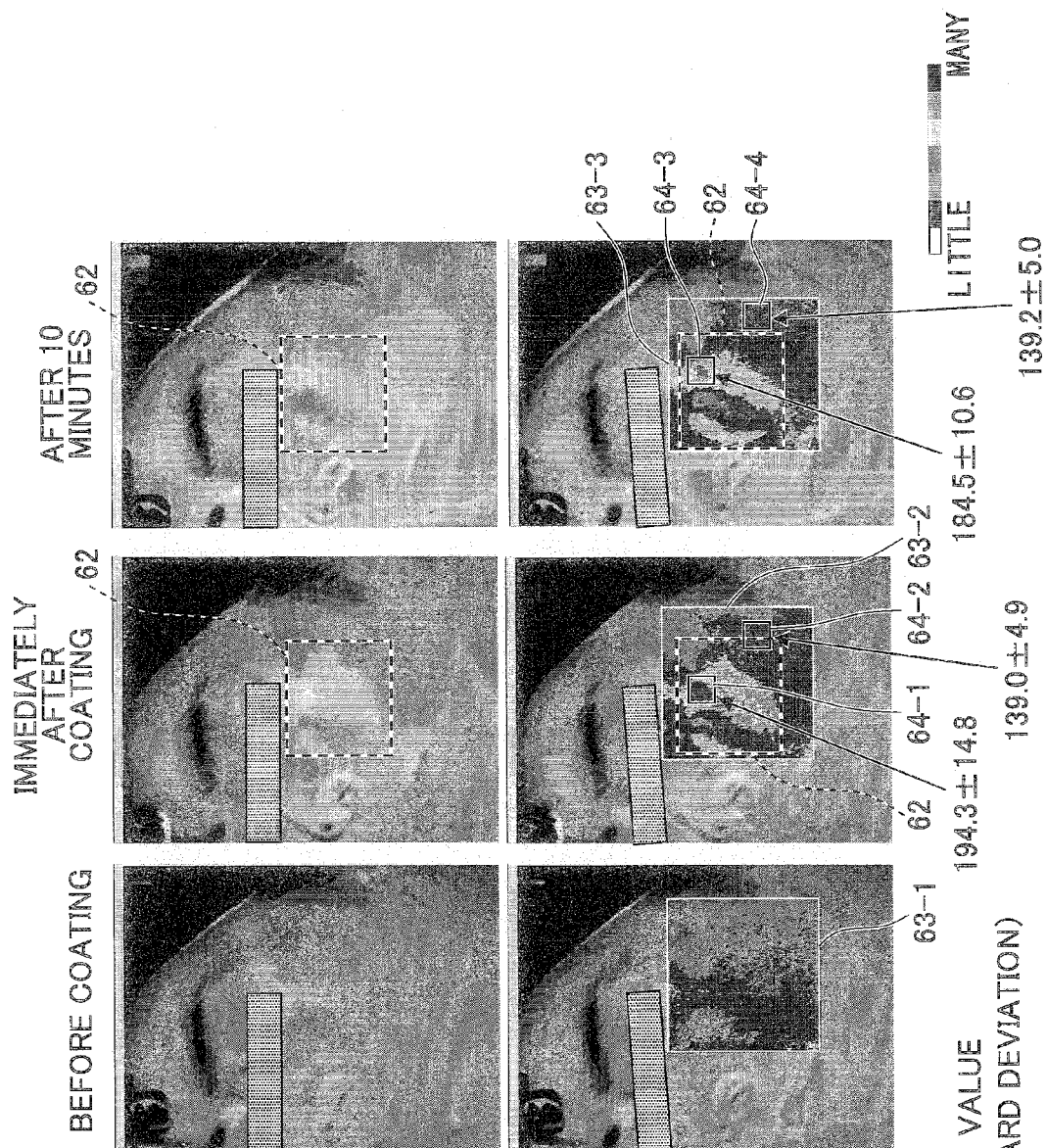
FIG. 16 illustrates luminance transitions before and after coating with emulsion in "water 2".

FIG. 16 illustrates luminance transitions in "water2" before and after coating with emulsion. FIG. 16 illustrates images obtained by imaging differences from the base image before, immediately after, and 10 minutes after coating, and images with pseudo-colors inside selected areas for emphasizing the differences. Further, referring to FIG. 16, differential images are calculated by subtracting the base image from an image of "water2" after correcting luminance in order to correct reflection on the skin surface to a certain extent.

Referring to FIG. 16, the coated area 62 is further coated with lotion. The user selects predetermined selected areas 63 using the input unit 41 such as a mouse (dragging the mouse). Pseudo-colors are set in the selected areas 63 by the image analyzing unit 45. Then, a result is displayed by the image forming unit 46.

Within the embodiment, the pseudo-colors are provided to display predetermined colors or patterns corresponding to the luminance differences. Said differently, depending on the values of the luminance transitions, pseudo-colors are displayed. The displayed pseudo-colors are synthesized with the facial image by overlapping the facial image. Therefore, it is possible to accurately know the location of and the level of the luminance differences.

Referring to FIG. 16, when the pseudo-color display on the selected area 63-1 before coating is compared with the pseudo-color display on the selected area 63-2 immediately after coating, the amount of the luminance transitions is greater in the selected area 63-2 than in the selected area 63-1. Further, when the pseudo-color display on the selected area 63-2 immediately after coating is compared with the pseudo-color display on the selected area 63-3 10 minutes after coating, the amount of the luminance transitions is smaller in the selected area 63-3 than in the selected area 63-2.

The differential image is obtained by subtracting the base image from the images of water or oil undergoing luminance correction. In the differential image, portions coated with water or oil are whitened. Because the emulsion is applied, the image "water2" is maintained after 10 minutes. This means that the emulsion remains on the skin.

When luminance transitions in the selected areas before and after coating with the lotion are calculated after performing several processes as in the above lotion, the value of the luminance transitions immediately after coating is 194.3±14.8 and the value of the luminance transitions on the luminance transition measuring area 64-2 is 139.0±4.9. Further, the value of the luminance transitions in the luminance transition measuring area 64-3 10 minutes after coating is 184.5±10.6 and the value of the luminance transitions in the luminance transition measuring area 64-4 may be 139.2±5.0.

The coated portions show luminance transitions in "oil", "water1", and "water2" immediately after coating. Although the value of the luminance transitions is greater in "water2" than in "water1", this may be caused due to the sensitivity or the imaging distance in the camera as described above. Although the luminance transitions decrease more in the images in "water1", "water2", and "oil" captured 10 minutes after coating than in the images in "water1", "water2", and "oil" captured immediately after coating, the emulsion sufficiently remains.

When portions other than the portions coated with the emulsion are viewed, there is almost no change in "oil". However, in "water2", increments of water can be observed more in the image 10 minutes after coating than in the image before coating because the luminance transitions increase after 10 minutes after coating. This phenomenon is probably caused by inherent function of skins. Because the emulsion is applied 10 minutes after washing the face, moisture may be once lost by the washing and subsequently recovered. This phenomenon is possibly due to this recovery of moisture (increment of water).

By using the plural images in the plural wavelength regions of the near-infrared region as described above, changes in water and oil are simultaneously traceable. Therefore, a sample containing water and oil such as emulsion can be simultaneously analyzed.

Figure 17:
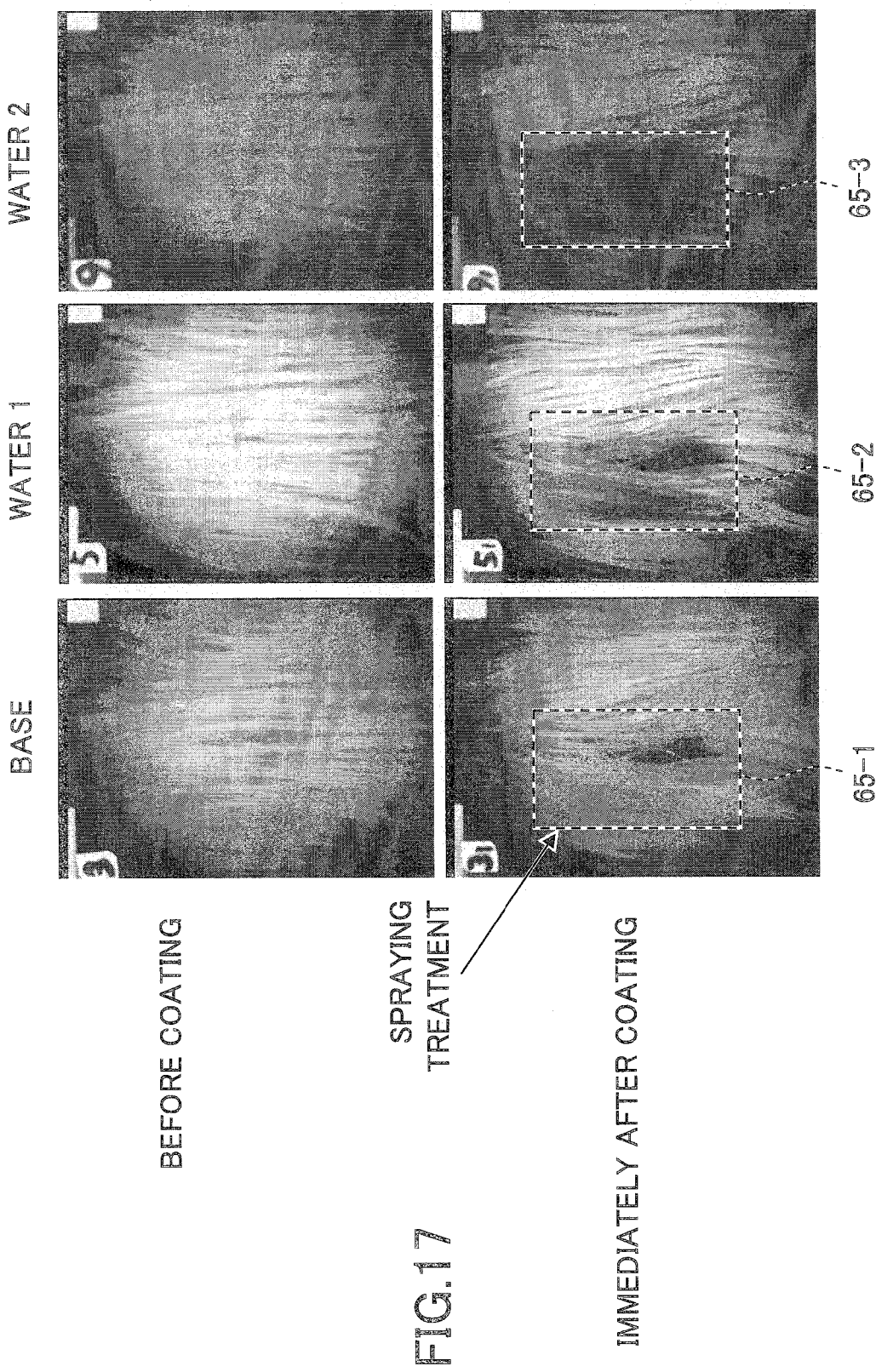
FIG. 17 illustrates exemplary head hair images before and after coating with hair treatment.

FIG. 17 illustrates exemplary head hair images before and after coating hair treatment. Referring to FIG. 17, the images of "base", "water1", "oil", and "water2" before, immediately after, and 10 minutes after coating are illustrated.

Here, the "base" is an image captured at a central wavelength of about 1300 nm±40 nm. The "water 1" is an image captured at a central wavelength of about 1500 nm±45 nm. The "water 2" is an image captured at a central wavelength of about 1920 nm±55 nm. Referring to FIG. 17, hair treatment as an external dermatological medication is applied on areas 61-1 to 61-4, and images are captured immediately after coating. The above luminance correction is applied to all images obtained above.

Referring to FIG. 17, the areas 62-1 to 62-3 correspond to coated areas of "base", "water1", and "water2", respectively. When water exists in a portion of the image, such portion is blacked (darkened) as in the coated areas 62-1 to 62-3.

Referring to FIG. 17, the rear of a head is directed toward the above lighting device 11. Water make the image blackened. Because moisture in hair is less in comparison with moisture in skin, an image of the hair becomes whitened. Here, an image of "base" shows a blackened portion immediately after spraying aquatic hair treatment. This is because the sprayed portion of the hair becomes wet and bunches so as to protrude from the other portions of the hair. Therefore, the wet portion possibly makes the image blackened.

Referring to FIG. 17, the sprayed portion is blackened by absorption of water in the images in "water1" and "water2".

Although the images in "water1" and "water2" are not similar, the non-similarity is possibly caused by the sensitivity relative to wavelengths or the imaging distance in the camera.

Next, a second embodiment is described. In the second embodiment, displays are devised so as to be easily understood by the user.

Figure 18:
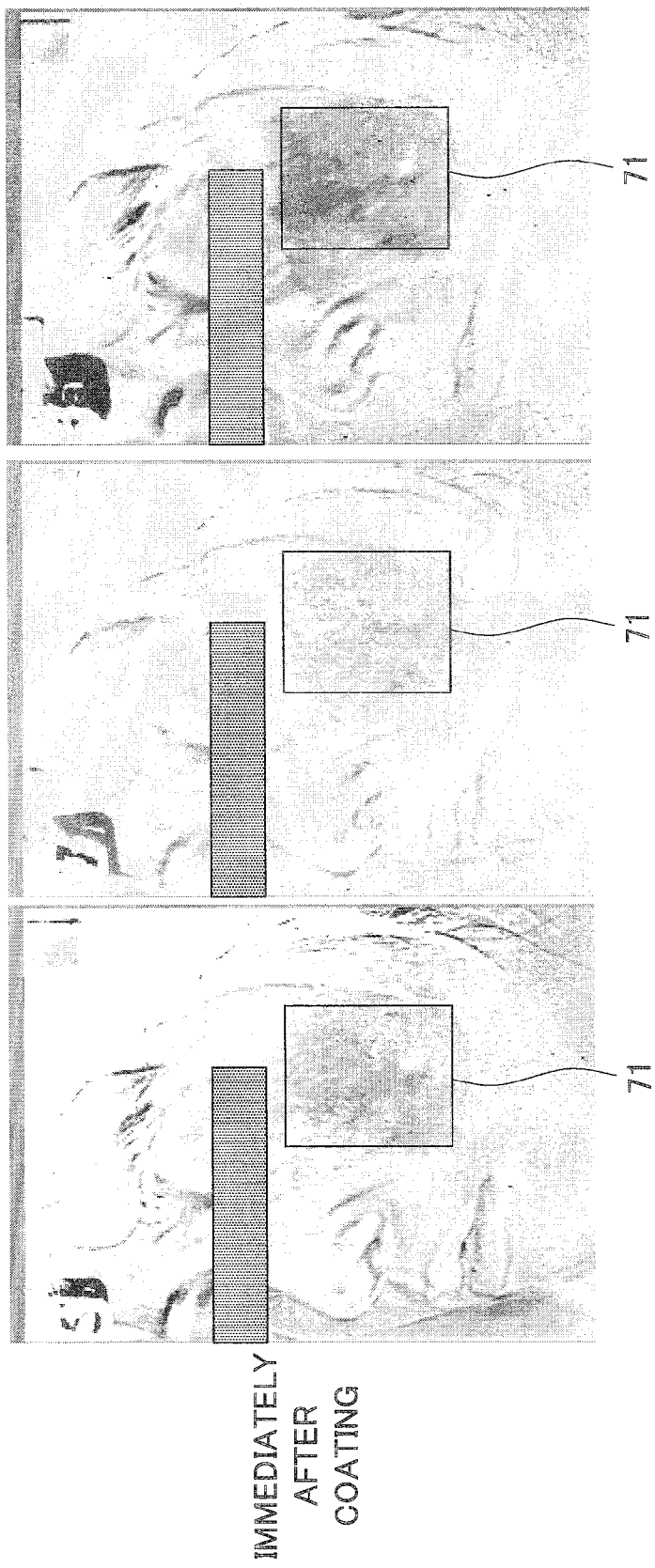
FIG. 18 illustrates exemplary luminance transitions before and after coating with lotion in another embodiment.
Figure 19:
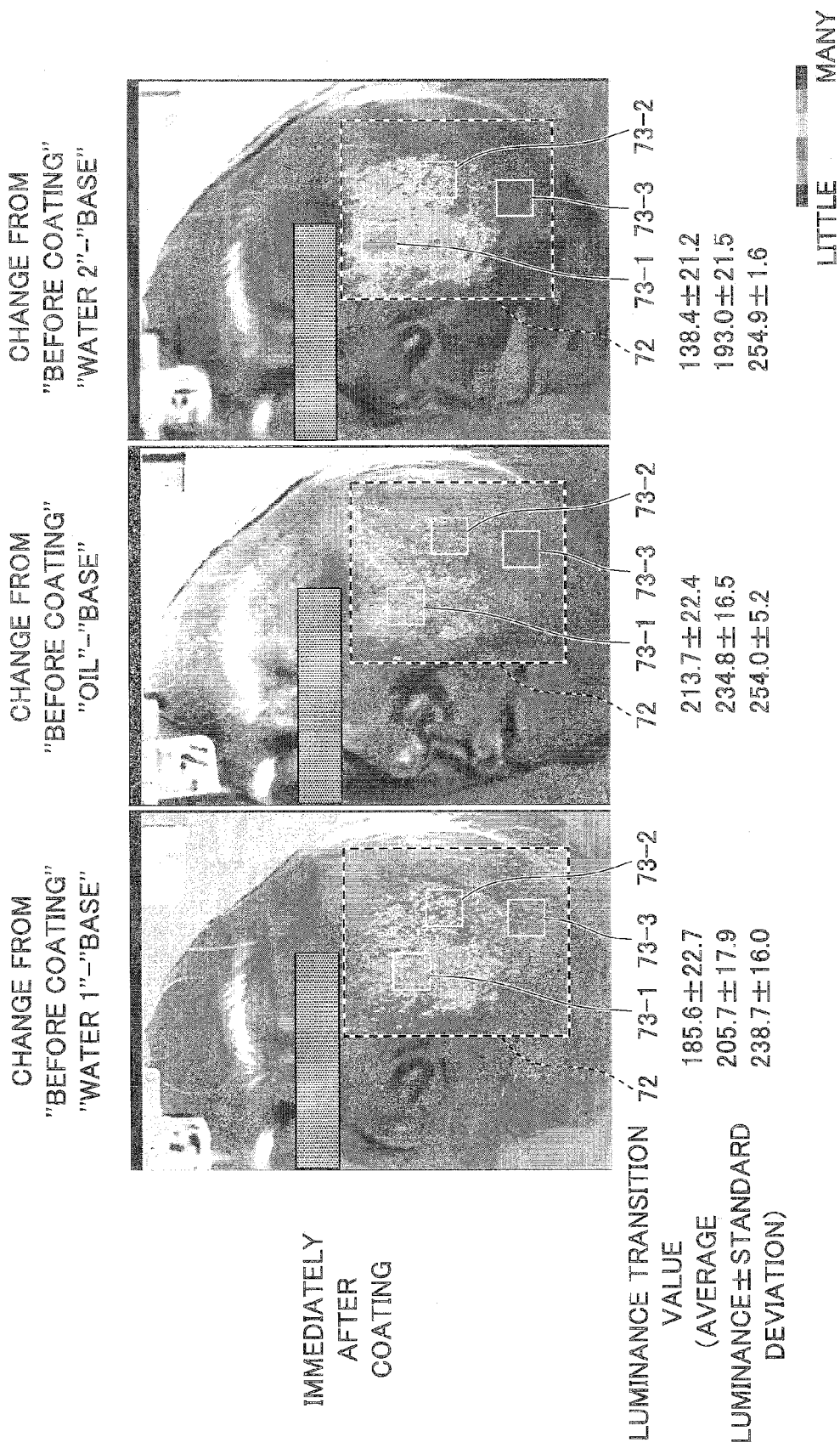
FIG. 19 is an exemplary pseudo-color display of selected areas corresponding to FIG. 18.

FIG. 18 illustrates exemplary luminance transitions before and after coating lotion in the second embodiment. FIG. 19 is an exemplary pseudo-color display of selected areas corresponding to FIG. 18.

Referring to FIGS. 18 and 19, luminance transitions between an image before coating and an image immediately after coating, e.g., "water1"-"base", "oil"-"base", and "water2"-"base", are illustrated. The lotion can be observed on coated areas 71 applied with an external dermatological medication. The colors of the differential images of the luminance transitions are changed between a case of "water1" and "water2" and a case of "oil". Referring to FIG. 18, the coated areas 71 are blackened which means that the difference value is great.

FIG. 19 illustrates a selected area to which the above pseudo-colors are allocated and luminance transition measuring areas 73-1 to 73-3 under various conditions. In a case of "water1"-"base", in the luminance transitions between the image before coating and the image immediately after coating, the luminance transition value in the luminance transition measuring area 73-1 is 185.6±22.7, the luminance transition value in the luminance transition measuring area 73-2 is 205.7±17.9, and the luminance transition value in the luminance transition measuring area 73-3 is 238.7±16.0. In a case of "oil"-"base", the luminance transition value in the luminance transition measuring area 73-1 is 213.7±22.4, the luminance transition value in the luminance transition measuring area 73-2 is 234.8±16.5, and the luminance transition value in the luminance transition measuring area 73-3 is 254.0±5.2. In a case of "water2"-"base", the luminance transition value in the luminance transition measuring area 73-1 is 138.4±21.2, the luminance transition value in the luminance transition measuring area 73-2 is 193.0±21.5, and the luminance transition value in the luminance transition measuring area 73-3 is 254.9±1.6.

Referring to FIG. 19, the luminance transitions are small in "oil" and great in "water1" and "water2". Further, it is known that the luminance transitions are greater in "water2" than in "water1".

Figure 20:
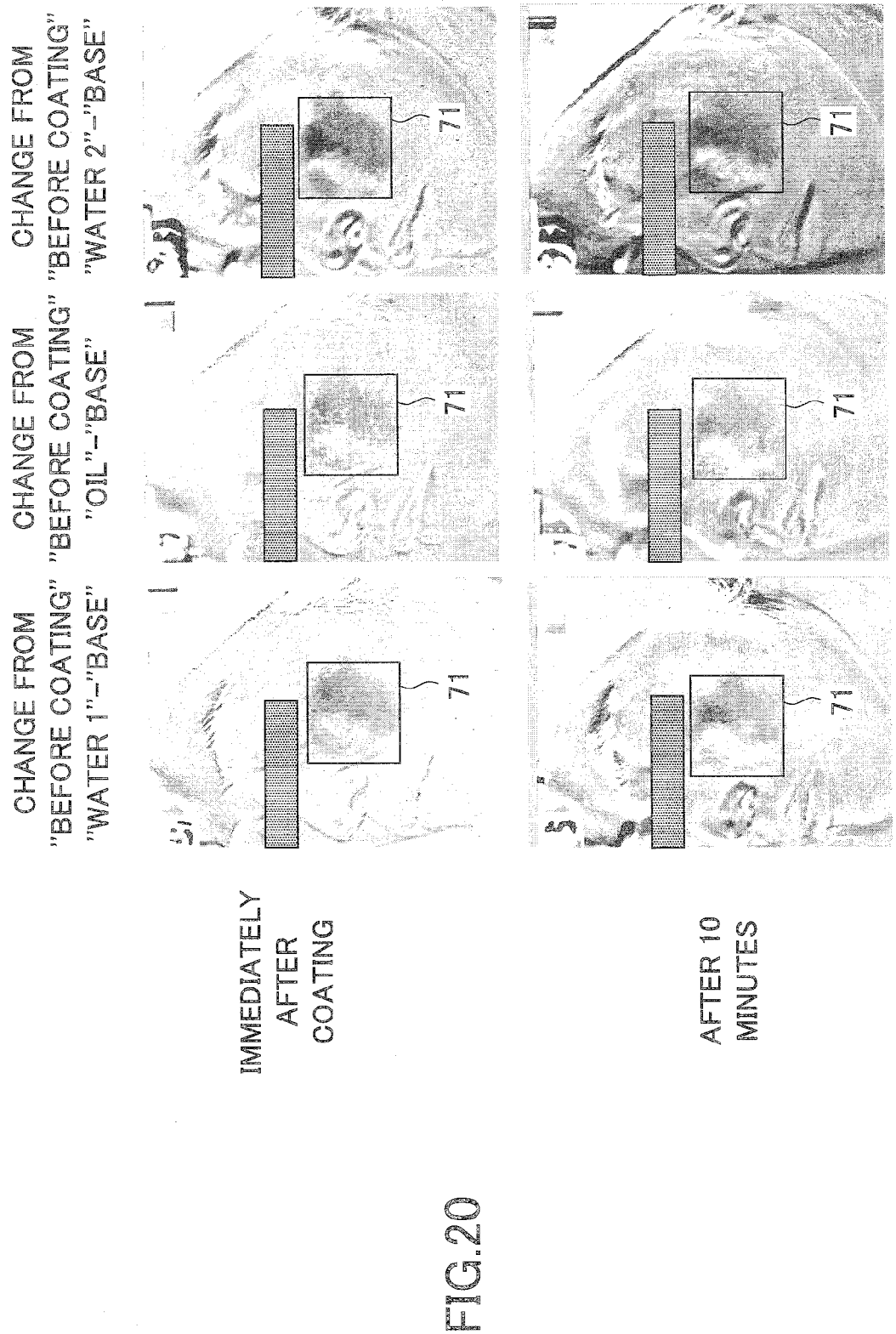
FIG. 20 illustrates exemplary luminance transitions before and after coating with lotion in another embodiment.
Figure 21:
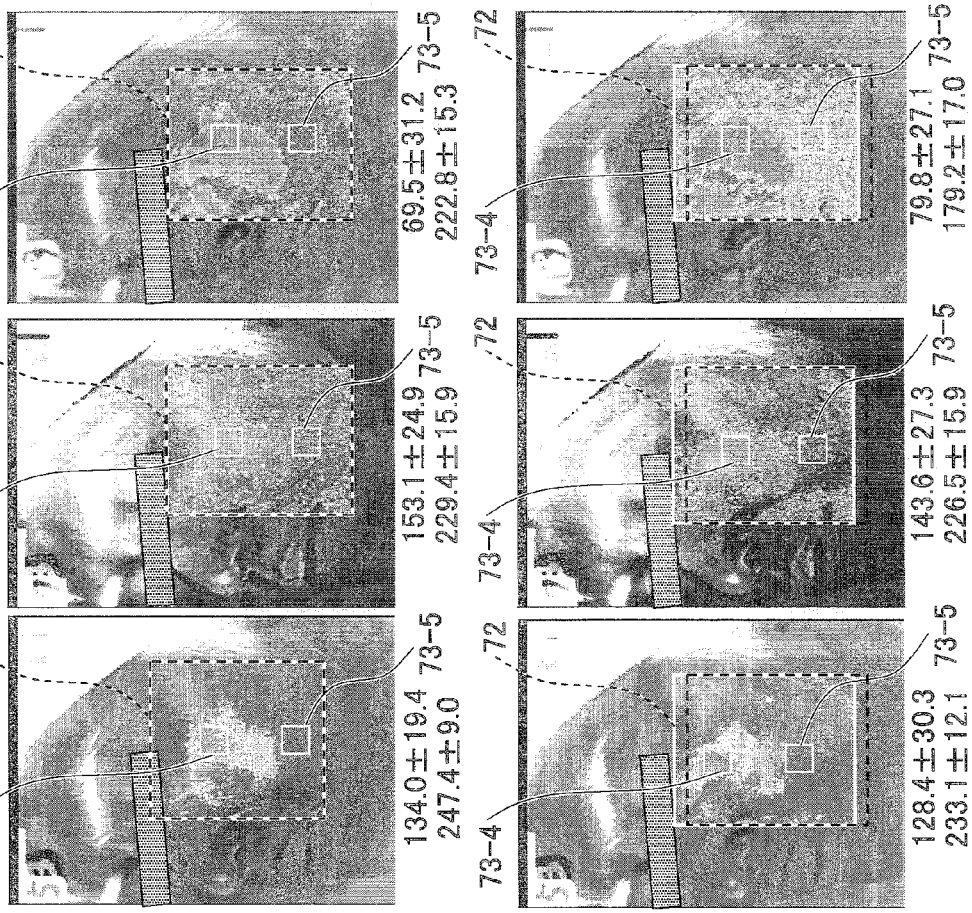
FIG. 21 is an exemplary pseudo-color display of selected areas corresponding to FIG. 20.

FIG. 20 illustrates exemplary luminance transitions before and after coating emulsion in the second embodiment. FIG. 21 is an exemplary pseudo-color display of selected areas corresponding to FIG. 20.

Referring to FIGS. 20 and 21, luminance transitions between an image immediately after coating and an image 10 minutes after coating, e.g., "water1"-"base", "oil"-"base", and "water2"-"base", are illustrated. The lotion can be observed on coated areas 71 applied with an external dermatological medication. The colors of the differential images of the luminance transitions are changed between a case of "water1" and "water2" and a case of "oil". Referring to FIG. 20, the coated areas 71 are darkened (blackened) which means that the difference value is great. Further, even 10 minutes after coating the emulsion, luminance transitions in an image immediately after coating and luminance transitions in an image 10 minutes after coating are similar.

FIG. 21 illustrates a selected area 72 to which the above pseudo-colors are allocated and luminance transition measuring areas 73-4 and 73-5 under various conditions. In a case of "water1"-"base", in a change from an image before coating the emulsion to an image immediately after coating, the luminance transition value in the luminance transition measuring area 73-4 is 134.0±19.4, and the luminance transition value in the luminance transition measuring area 73-5 is 247.4±9.0. In a change from the image before coating the emulsion to an image 10 minutes after coating, the luminance transition value in the luminance transition measuring area 73-4 is 128.4±30.3, and the luminance transition value in the luminance transition measuring area 73-5 is 233.1±12.1.

In a case of "oil"-"base", in a change from the image before coating the emulsion to an image immediately after coating, the luminance transition value in the luminance transition measuring area 73-4 is 153.1±24.9, and the luminance transition value in the luminance transition measuring area 73-5 is 229.4±15.9. In a change from the image before coating the emulsion to an image 10 minutes after coating, the luminance transition value in the luminance transition measuring area 73-4 is 143.6±27.3, and the luminance transition value in the luminance transition measuring area 73-5 is 226.5±15.9.

In a case of "water2"-"base", in a change from the image before coating the emulsion to an image immediately after coating, the luminance transition value in the luminance transition measuring area 73-4 is 69.5±31.2, and the luminance transition value in the luminance transition measuring area 73-5 is 222.8±15.3. In a change from the image before coating the emulsion to an image 10 minutes after coating, the luminance transition value in the luminance transition measuring area 73-4 is 79.8±27.1, and the luminance transition value in the luminance transition measuring area 73-5 is 179.2±17.0.

As described, by presenting the luminance transition values for luminance transition measuring areas designated by a user, it is possible to easily inform the user of a changed value for an arbitrary place. Thus, the user can easily understand the differences of the luminance.

The above images can be easily presented to the subject or the user, counseling on makeup can be conducted while applying an external dermatological medication using the evaluating unit 48 or the image analysis device 12.

Further, the obtained images may be managed and stored for each subject. The stored data are statistically processed so as to temporally evaluate the makeup. Further, by using the four wavelengths, skin, hair or the like is analyzed.

As described, the images in the near-infrared region can be accurately captured in the embodiments. Therefore, skin or the like can be highly accurately analyzed using the images in the near-infrared region. Further, within the embodiments, it is possible to check a state of water existing in abase substance, to image a state of water depending on applications, and to analyze an expanded image of skin, a coated state of water in cristae and sulci, an expanded image of hair, moisture in nail, or the like.

Further, within the embodiments, it is possible to conduct counseling by a counselor where and how cosmetics are better applied for each user or to use in evaluating beauty regimens.

Specifically, the embodiments can be applied to methods for evaluating makeup cosmetics such as evaluation of a washing effect of a cleaning liquid or evaluation of adhesion of foundation (FD) by analyzing moisture distribution using near-infrared images and evaluating exposed skin.

Further, the embodiments are applicable to a new skin type classification using distribution analysis for a specific ingredient by near-infrared images such as a skin type evaluation method using distribution of water and oil, an evaluation program by analyzing distribution of water and oil using the near-infrared images, a moisturizing action evaluating method of cleaning liquid, and a moisturizing action evaluating method of cleaning liquid by analyzing moisture distribution using the near-infrared images.

Next, an evaluation method of evaluating a moisture change in skin of a subject and a change of adhesion of cosmetics using the above evaluating unit 48 is described.

The evaluating unit 48 can evaluate a washing effect of cleaning liquid by analyzing moisture distribution using near-infrared images and evaluating exposed skin based on a result obtained by the above image analyzing unit 45.

Example 1 of the above evaluation method is described. Within the example 1, effects of cleansing products on a skin coated with a foundation (FD) are compared using a near-infrared imaging method.

A method of evaluating the washing effect is performed by coating the left and right cheeks of a user with the same foundation, pushing cotton pieces respectively soused by different cleansing products of about 2 ml respectively against the left and right cheeks for about 10 seconds, and removing the excessive cleansing products by wipe.

Figure 22:
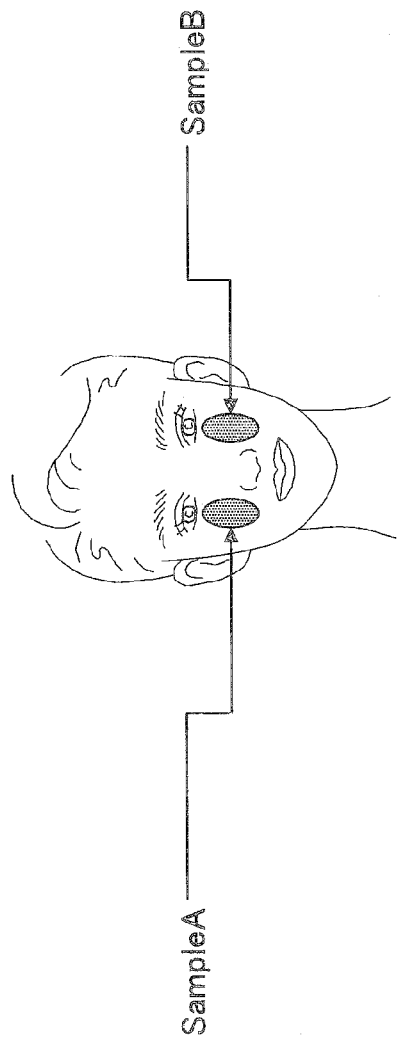
FIG. 22 illustrates how two samples of the example 1 of the present invention are prepared.

FIG. 22 illustrates how the two cleansing products are applied in the evaluation method of the example 1. FIG. 22 illustrates various conditions for applying samples A and B (the foundation products) respectively applied to the right and left cheeks of the user before coating, during coating, during cleansing, immediately after cleansing, and 15 minutes after cleansing. After preparing as illustrated in FIG. 22, images are captured before coating, during coating, during cleansing, immediately after cleansing, and 15 minutes after cleansing in wavelength regions such as 1950 nm, 1775 nm, 1500 nm, 1460 nm and 1300 nm of the near-infrared region.

Next, within the example 1, the near-infrared camera 24 illustrated in FIG. 2 is used to capture images before coating with the foundation, after coating with the foundation, immediately after processing as described above, and 15 minutes after processing as described above. The image captured 15 minutes after processing is obtained to check a state without excessive moisture.

Figure 23:
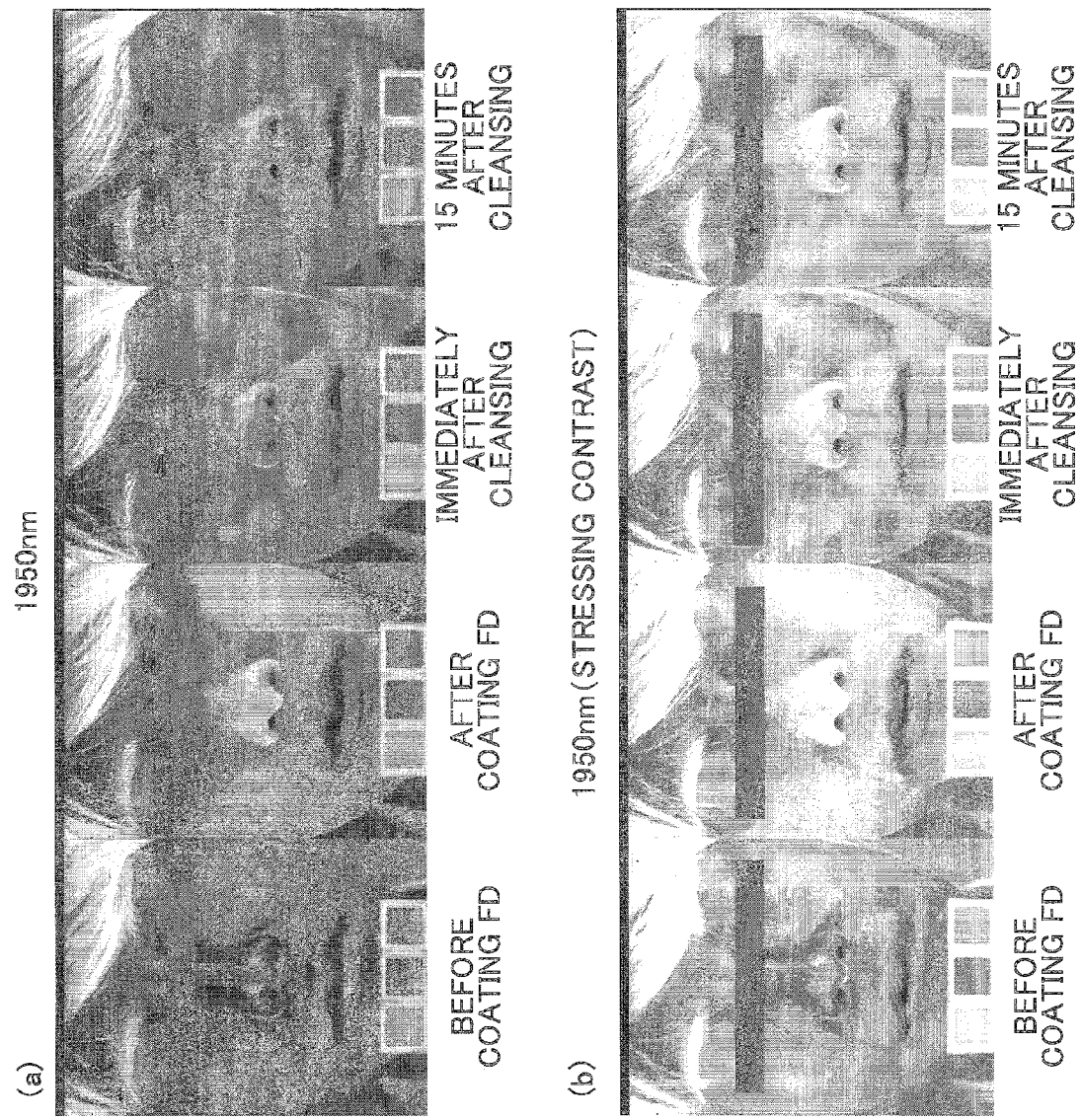
FIG. 23 illustrates exemplary images captured under the conditions of the example 1.
Figure 24:
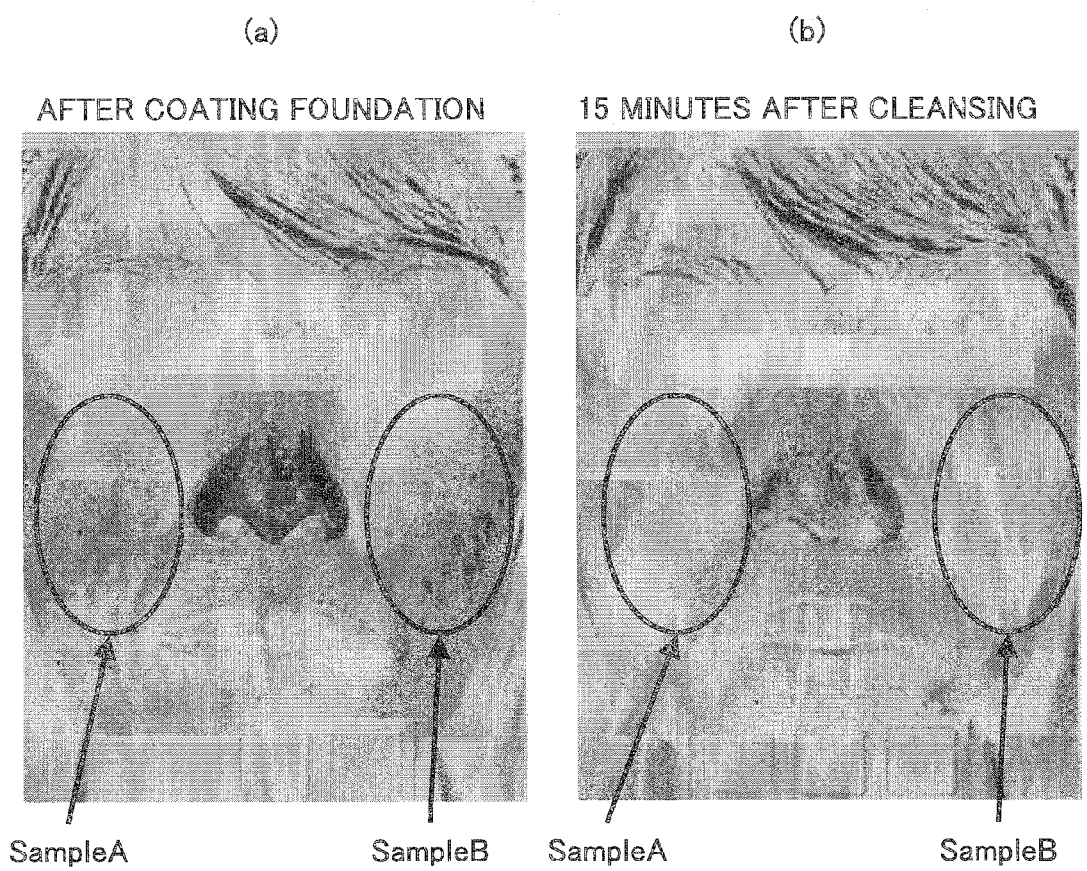
FIG. 24 illustrates evaluation results under the conditions of the example 1.

FIG. 23 illustrates exemplary images captured under conditions of the example 1. FIG. 24 illustrates evaluation results under conditions of the example 1. Referring to (a) and (b) of FIG. 23, facial images are captured in the wavelength region of about 1950 nm of the near-infrared region before coating with the foundation, after coating with the foundation, immediately after cleansing, and 15 minutes after cleansing. The images are processed using the color chart corresponding to the wavelength region of the near-infrared region among the above-described three color charts having different reflection coefficients. Referring to FIG. 23, the images (b) are emphasized to stress contrast by a predetermined image processing in comparison with the images (a).

From the images (a) and (b), it is possible to easily know conditions of the skin. By adjusting the contrast of the images (b), it is possible to further clearly know differences of the conditions of the skin.

Referring to FIG. 24, the washing effect is imaged by the near-infrared camera 22. Referring to FIG. 24, an image (a) captured after coating with the foundation is blackened at the samples A and B. In an image (b) captured 15 minutes after cleansing, the sample A is slightly blackened but the sample B is not blackened. Therefore, it is possible to evaluate that the sample B has a better washing effect than the sample A.

The evaluating unit 48 can evaluate adhesion of cosmetics by analyzing moisture distribution using near-infrared images and evaluating exposed skin based on a result obtained by the above image analyzing unit 45.

Example 2 of the above evaluation method is described next. Within the example 2, a temporal change after coating with foundation is observed using a near-infrared imaging method.

Before evaluating the adhesion of the foundation, foundations having different durability are respectively applied to left and right cheeks. Next, the near-infrared camera is used to capture images before coating with the foundations, immediately after coating with the foundation, and 60 minutes after coating with the foundation.

Figure 25:
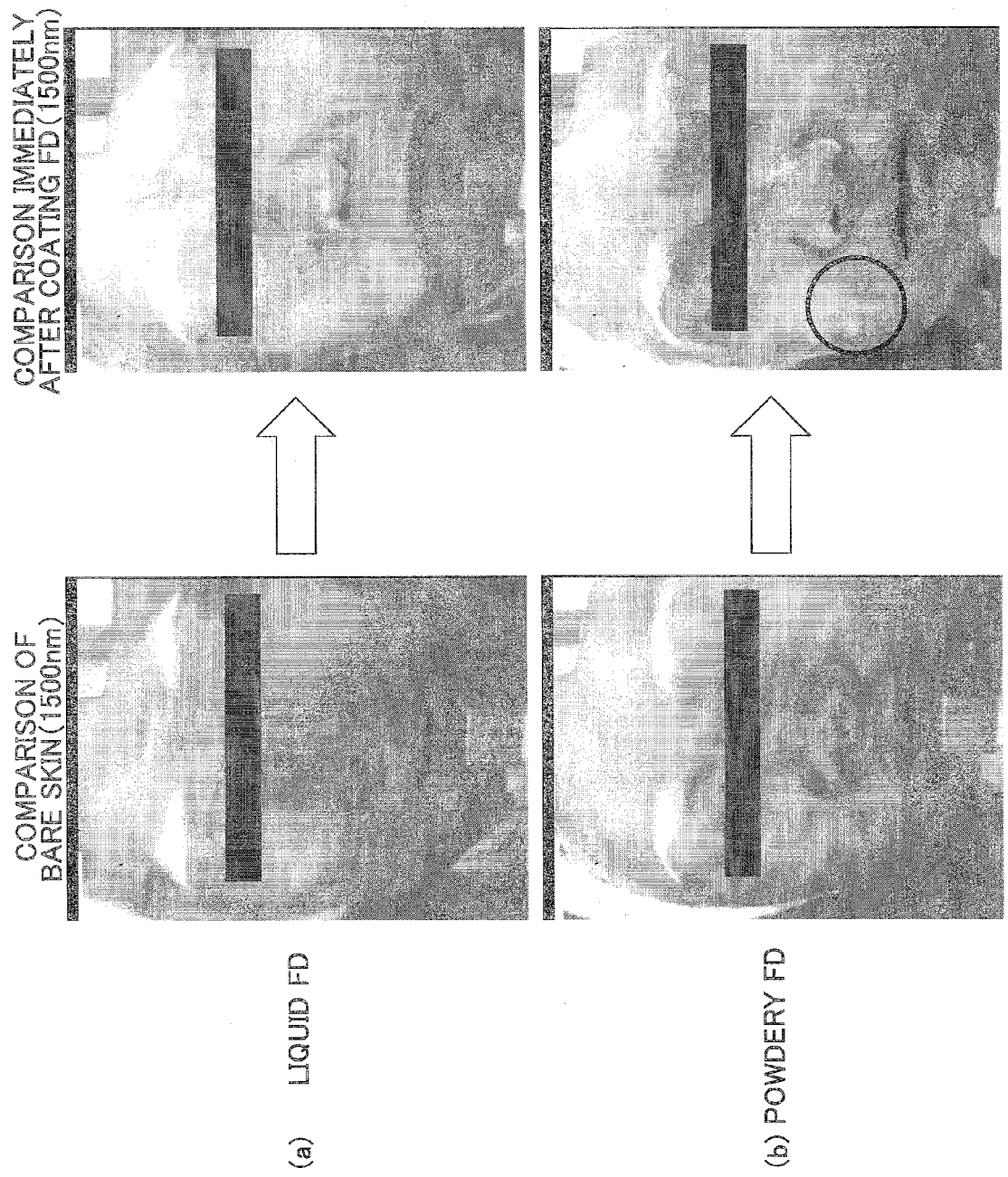
FIG. 25 illustrates exemplary images obtained under conditions of an example 2.

FIGS. 25 to 28 illustrate images 1 to 4 obtained under the conditions of the example 2. Referring to FIG. 25, images (a) captured when liquid foundation (FD) is applied are compared with images (b) captured when powdery foundation (FD) is applied immediately after applying the foundations. Referring to FIG. 25, the images (a) and (b) are captured in a wavelength region of about 1500 nm of the near-infrared region.

In the images (a), since the liquid foundation is applied, the image becomes whitened. In the images (b), since the powdery foundation is applied, the image becomes whitened and unevenness in coating with the powdery foundation is observed as gray. Therefore, it is possible to evaluate the adhesion of the foundation by using the images in FIG. 25.

Figure 26:
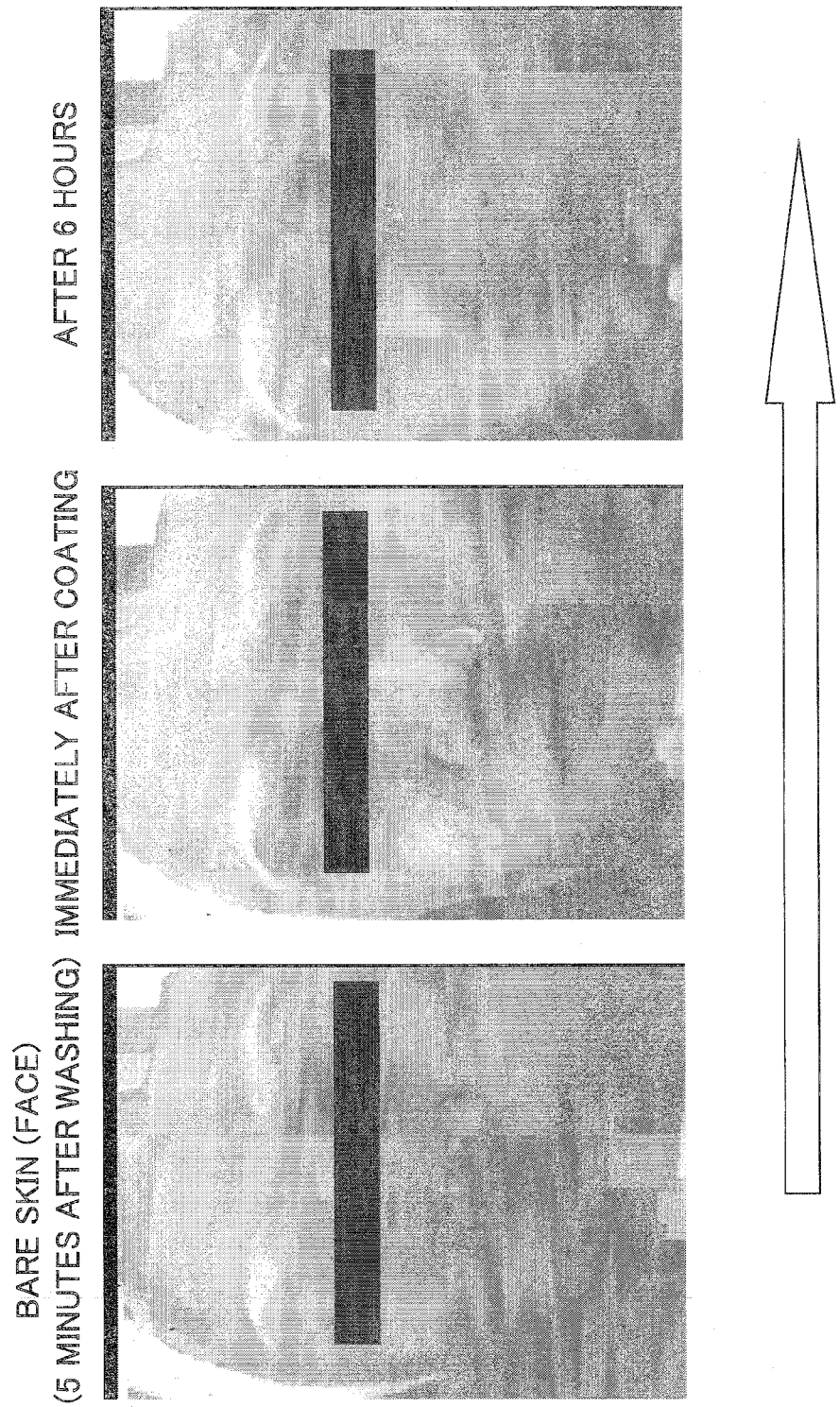
FIG. 26 illustrates exemplary images obtained under the conditions of the example 2.

Further, referring to FIG. 26, the temporal changes of the adhesion of the foundation 5 minutes after washing the face (natural face), immediately after coating with the foundation, and 6 hours after coating with the foundation are observed. With this, white portions observed immediately after coating with the foundation change to gray. Said differently, by analyzing the images as illustrated in FIG. 26, it is possible to determine whether the foundation is fixed and it is possible to evaluate adhesion of each foundation.

Figure 27:
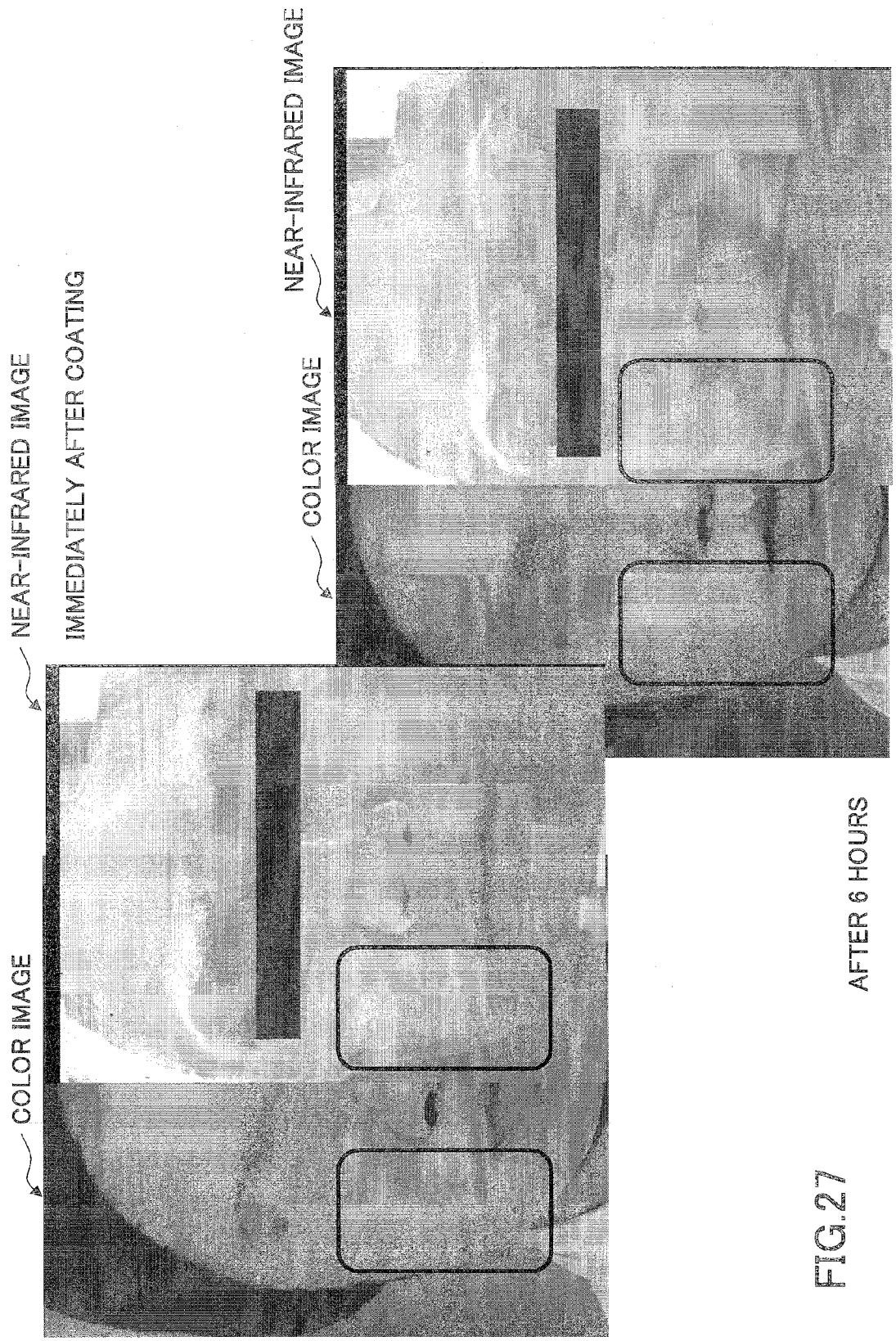
FIG. 27 illustrates exemplary images obtained under the conditions of the example 2.

Further, as illustrated in FIG. 27, skin images of cheeks captured immediately after coating and 6 hours after coating are compared. In comparison with an ordinary photo (a color photo), the image captured in the near-infrared region (a near-infrared region image) makes the image distinguishable. Thus, by using the near-infrared region image as illustrated in FIG. 27, an appropriate evaluation becomes possible.

Further, referring to FIG. 28, in the example 2, when a state of applying makeup cosmetics is imaged by the above image forming unit 46, it is possible to generate an image (a) with and without makeup respectively in a right face and a left face. Further, as in an image (b), a near-infrared camera image can be generated. Furthermore, as in an image (c), a color image having pseudo-colors at changed portions of coated conditions of the cosmetics can be generated. By appropriately displaying the generated images (a), (b), and (c) of FIG. 28, the adhesion of the foundation can be highly accurately evaluated.

As described, the evaluating unit 48 of the second embodiment can analyze the images and highly accurately evaluate the moisturizing action and the adhesion of the cosmetics. The evaluating unit may evaluate any one or both of the moisturizing action and the adhesion of the cosmetics. For example, contents of the evaluation may be predetermined depending on the user or the like or the subject.

As described, within the embodiments, skin or the like can be highly accurately analyzed using images in the near-infrared region. Further, a highly accurate evaluation for skin or the like can be performed from the result of the analysis.

Within the embodiments, it is possible to check a state of water existing in the base substance, to image a state of water depending on applications, and to analyze an expanded image of skin, a coated state of water in cristae and sulci, an expanded image of hair, moisture in nail, or the like.

Further, within the embodiments, it is possible to conduct counseling by a counselor where and how cosmetics are better applied for each user or to use in evaluating beauty regimens.

Specifically, the embodiments are applicable to analysis of moisture distribution using near-infrared images, the washing effect of cleaning liquid can be analyzed by evaluating exposed skin, and the adhesion of makeup cosmetics can be evaluated by analyzing moisture distribution using near-infrared images and evaluating exposed skin.

Further, the embodiments are applicable to the new skin type classification using distribution analysis for the specific ingredient by near-infrared images such as the skin type evaluation method using distribution of water and oil, the evaluation program by analyzing distribution of water and oil using the near-infrared images, the moisturizing action evaluating method of cleaning liquid, and the moisturizing action evaluating method of cleaning liquid by analyzing moisture distribution using the near-infrared images.

Further, within the embodiments, it is possible to conduct counseling by a counselor where and how cosmetics are better applied for each user or to use in evaluating beauty regimens.

Although the invention has been described with respect to specific embodiments for a complete and clear disclosure, the appended claims are not to be thus limited but are to be construed as embodying all modifications and alternative constructions that may occur to one skilled in the art that fairly fall within the basic teachings herein set forth.

This international patent application is based on Japanese Priority Patent Application No. 2010-52189 filed on Mar. 9, 2010, Japanese Priority Patent Application No. 2010-52190 filed on Mar. 9, 2010, Japanese Priority Patent Application No. 2010-199388 filed on Sep. 6, 2010, and Japanese Priority Patent Application No. 2010-199389 filed on Sep. 6, 2010, the entire contents of which are hereby incorporated herein by reference.

The invention claimed is:

1. A lighting device for capturing a facial image of a subject by an image capturing unit in a plurality of different near-infrared regions of light, the lighting device comprising:
   a housing in which a substantially spherical space is formed by a spherical surface, the housing being configured to accommodate an entire face part of the subject;
   at least two light sources arranged at positions bilaterally symmetrical with respect to the subject on the spherical surface to emit the light to light the substantially spherical space in the housing;
   an image capturing unit configured to capture an image of the entire face part lighted by the light;
   a first filter installed in front of the light source to block ultraviolet rays and infrared rays from the emitted light;
   a second filter installed in front of the lens of the image capturing unit to adjust an amount of the light, and
   a third filter installed in front of the lens of the image capturing unit to perform band-pass filtering corresponding to the plurality of different near-infrared regions.

2. The lighting device according to claim 1, further comprising:
   a first shield installed inside the housing to prevent the light emitted by the light source from directly lighting the subject.

3. The lighting device according to claim 1, further comprising:
   a second shield provided on a front periphery of the lens of the image capturing unit.

4. The lighting device according to claim 1, further comprising:
   a filter sliding mechanism configured to exchange the second shield and the third shield.

5. The lighting device, according to claim 1, wherein an inside of the housing is recoated by a predetermined paint.

6. The lighting device according to claim 1, wherein the light source is a halogen light source or an LED used for capturing the facial image in the near-infrared regions of the light.

7. An image analysis device for analyzing skin or hair of a subject using a facial image of the subject in a plurality of different near-infrared, regions captured by a lighting device, the image analysis device comprising:
   an image acquiring unit configured to acquire the facial images before and after coating with an external dermatological medication on the skin or the hair of the subject;
   a luminance correcting unit configured to correct luminance of the facial image acquired by the image acquiring unit;
   a difference amount acquiring unit configured to acquire difference amounts of the corrected facial images acquired by the luminance correcting unit before and after coating with the external dermatological medication on the skin or the hair of the subject in each of the plurality of near-infrared regions;
   an analyzing unit configured to analyze the skin and the hair of the subject based on the difference amounts acquired by the difference amount acquiring unit; and
   an image forming unit configured to generate an image for displaying a result of analysis acquired by the analyzing unit.

8. The image analysis device according to claim 7, wherein the plurality of near-infrared regions are at least two ranges among a range of 1100 nm to 1360 nm, a range of 1300 nm to 1640 nm, a range of 1860 nm to 2200 nm, a range of 1700 nm to 1860 nm, and a range of 2230 nm to 2400 nm.

9. The image analysis device according to claim 7, wherein the image forming unit generates a screen highlighted by a predetermined color or a predetermined pattern for each predetermined pixel based on the difference amounts acquired by the difference amount acquiring unit.

10. The image analysis device according to claim 7, wherein the analyzing unit calculates a luminance transition value for a predetermined area set by a user on the image generated by the image forming unit to display the result of analysis.

11. The image analysis device according to claim 7, further comprising:
    an evaluating unit configured to evaluate moisturizing action for the skin or the hair of the subject with a cleaning liquid or adhesion of a cosmetic based on the result of analysis acquired by the analyzing unit.

12. An image analysis method for analyzing skin or hair of a subject using a facial image of the subject captured in a plurality of different near-infrared regions, the image analysis method comprising:
    acquiring the facial images before and after coating with an external dermatological medication on the skin or the hair of the subject;

correcting luminance of the facial image acquired by the acquiring the facial images;

acquiring difference amounts of the corrected facial images acquired by the correcting before and after coating with the external dermatological medication on the skin or the hair of the subject in each of the plurality of near-infrared regions;

analyzing the skin and the hair of the subject based on the difference amounts acquired by the acquiring the difference amounts; and generating an image for displaying a result of analysis acquired by the analyzing the skin and the hair.

13. The image analysis method according to claim 12, wherein the plurality of near-infrared regions are at least two ranges among a range of 1100 nm to 1360 nm, a range of 1300 nm to 1640 nm, a range of 1860 nm to 2200 nm, a range of 1700 nm to 1860 nm, and a range of 2230 nm to 2400 nm.

14. The image analysis method according to claim 12, wherein the generating the image generates a screen highlighted by a predetermined color or a predetermined pattern for each predetermined pixel based on the difference amounts acquired by the difference amount acquiring unit.

15. The image analysis method according to claim 12, wherein the analyzing the skin and the hair calculates a luminance transition value for a predetermined area set by a user on the image generated by the generating the image.

16. An evaluation method according to claim 12, further comprising:

evaluating moisturizing action for the skin or the hair of the subject with a cleaning liquid or adhesion of a cosmetic based on the result of analysis acquired by the analyzing the skin and the hair.

* * * * *